US012692519B2

(12) United States Patent
Milo et al.

(10) Patent No.: US 12,692,519 B2
(45) Date of Patent: Jul. 28, 2026

(54) ENGINEERED AUTOTROPHIC BACTERIA FOR CO₂ CONVERSION TO ORGANIC MATERIALS

(71) Applicant: Yeda Research and Development Co. Ltd., Rehovot (IL)

(72) Inventors: Ron Milo, Kfar-Saba (IL); Shmuel Gleizer, Rehovot (IL); Niv Antonovsky, Rehovot (IL); Elad Noor, Rehovot (IL); Arren Bar-Even, Rehovot (IL); Yehudit Zohar, Rehovot (IL); Roee Ben Nissan, Rehovot (IL); Elad Herz, Rehovot (IL); Yinon Moise Bar-On, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 785 days.

(21) Appl. No.: 17/768,228

(22) PCT Filed: Oct. 22, 2020

(86) PCT No.: PCT/IL2020/051109
§ 371 (c)(1),
(2) Date: Apr. 12, 2022

(87) PCT Pub. No.: WO2021/084526
PCT Pub. Date: May 6, 2021

(65) Prior Publication Data
US 2024/0117386 A1      Apr. 11, 2024

Related U.S. Application Data

(60) Provisional application No. 62/928,385, filed on Oct. 31, 2019.

(51) Int. Cl.

| | |
|---|---|
| *C12P 1/04* | (2006.01) |
| *C07K 14/195* | (2006.01) |
| *C12N 1/20* | (2026.01) |
| *C12N 9/02* | (2006.01) |
| *C12N 9/12* | (2006.01) |
| *C12N 9/88* | (2006.01) |

(52) U.S. Cl.
CPC .............. *C12P 1/04* (2013.01); *C07K 14/195* (2013.01); *C12N 1/20* (2013.01); *C12N 9/0008* (2013.01); *C12N 9/1205* (2013.01); *C12N 9/88* (2013.01); *C12Y 102/02001* (2013.01); *C12Y 207/01019* (2013.01); *C12Y 401/01039* (2013.01); *C12Y 402/01001* (2013.01)

(58) Field of Classification Search
None
See application file for complete search history.

(56) References Cited

U.S. PATENT DOCUMENTS

| | | | | |
|---|---|---|---|---|
| 9,410,131 | B2 * | 8/2016 | Milo ............. | C12Y 401/01031 |
| 10,077,437 | B2 * | 9/2018 | Milo .................. | C12N 9/1018 |
| 10,294,482 | B2 * | 5/2019 | Milo .................. | C12Y 504/02 |
| 12,031,138 | B2 * | 7/2024 | Milo .................. | C07K 14/245 |
| 2017/0183665 | A1 * | 6/2017 | Milo .................. | C07K 14/195 |

FOREIGN PATENT DOCUMENTS

| | | |
|---|---|---|
| WO | WO 2009/062190 | 5/2009 |
| WO | WO 2011/088425 | 7/2011 |
| WO | WO 2013/123454 | 8/2013 |
| WO | WO 2021/084526 | 5/2021 |

OTHER PUBLICATIONS

Kizer et al. Appl Environ Microbiol. May 2008;74(10):3229-41. (Year: 2008).*
Prather et al. Curr Opin Biotechnol. Oct. 2008;19(5):468-74. (Year: 2008).*
Chica et al. Curr Opin Biotechnol. Aug. 2005;16(4):378-84. (Year: 2005).*
Singh et al. Curr Protein Pept Sci. 2017, 18, 1-11 (Year: 2017).*
International Search Report and the Written Opinion Dated Feb. 5, 2021 From the International Seaching Authority Re. Application No. PCT/IL2020/051109. (14 Pages).
Antonovsky et al. "Sugar Synthesis From CO2 in *Escherichia coli*", Cell, XP029627883, 166(1): 115-125, Published Online Jun. 23, 2016.
Gleizer et al. "Conversion of *Escherichia coli* to Generate All Biomass Carbon From CO2", Cell, XP085925062, 179(6): 1255-1263, Nov. 27, 2019.
Herz et al. "The Genetic Basis for the Adaptation of *E. coli* to Sugar Synthesis From CO2", Nature Communications, XP055768067, 8(1): 1705-1-1705-10, Published Online Nov. 22, 2017.
Mattozzi et al. "Expression of the Sub-Pathways of the Chloroflexus Aurantiacus 3-Hydroxypropionate Carbon Fixation Bicycle in *E. coli*: Toward Horizontal Transfer of Autotrophic Growth", Metabolic Engineering, XP055568085, 16: 130-139, Available Online Jan. 29, 2013.

* cited by examiner

*Primary Examiner* — Christian L Fronda

(57) ABSTRACT

A recombinant bacteria which is genetically modified to express formate dehydrogenase (FDH), phosphoribulokinase (prk) and Ribulose-Bisphosphate Carboxylase/oxygenase (RuBisCo) is disclosed. The bacteria may be modified to be autotrophic.

9 Claims, 17 Drawing Sheets

Specification includes a Sequence Listing.

FIG. 2B

FIG. 4

Figure 6A:
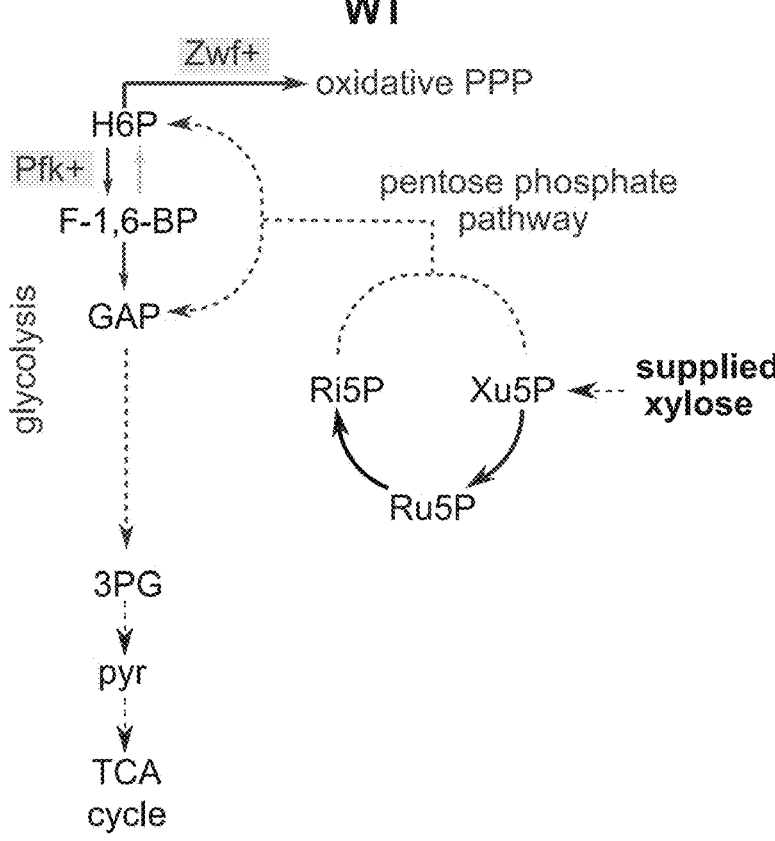
Figure 6B:
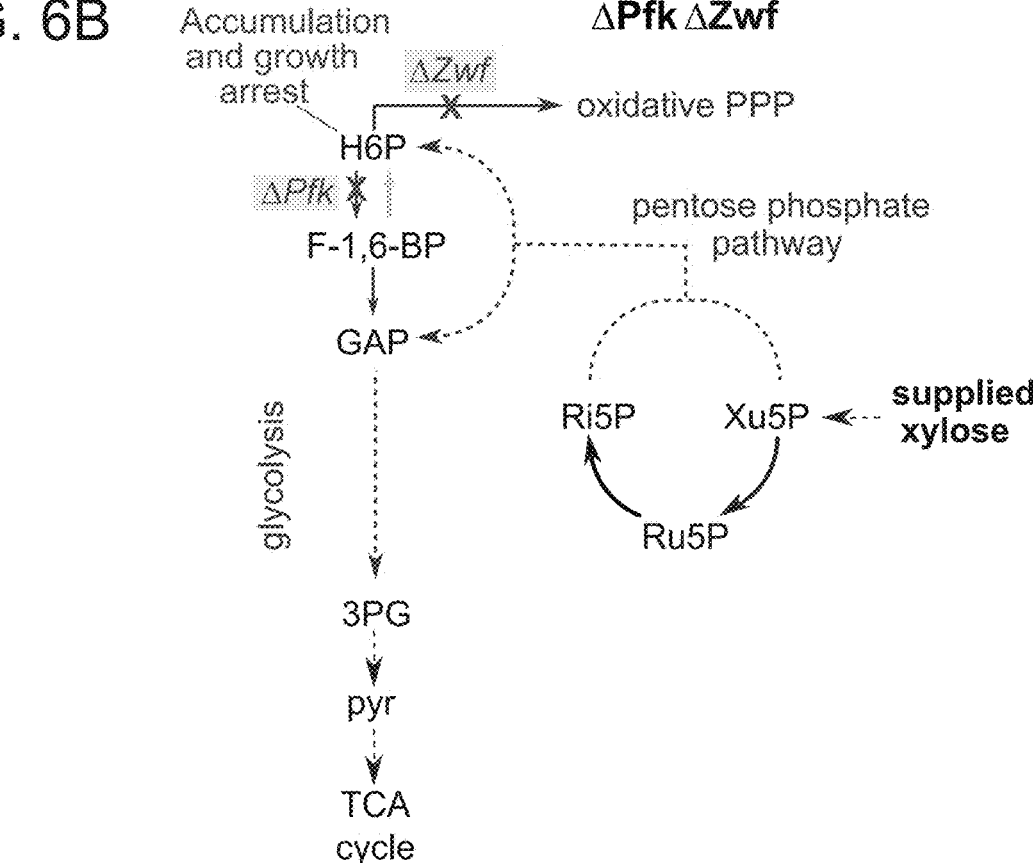
Figure 6C:
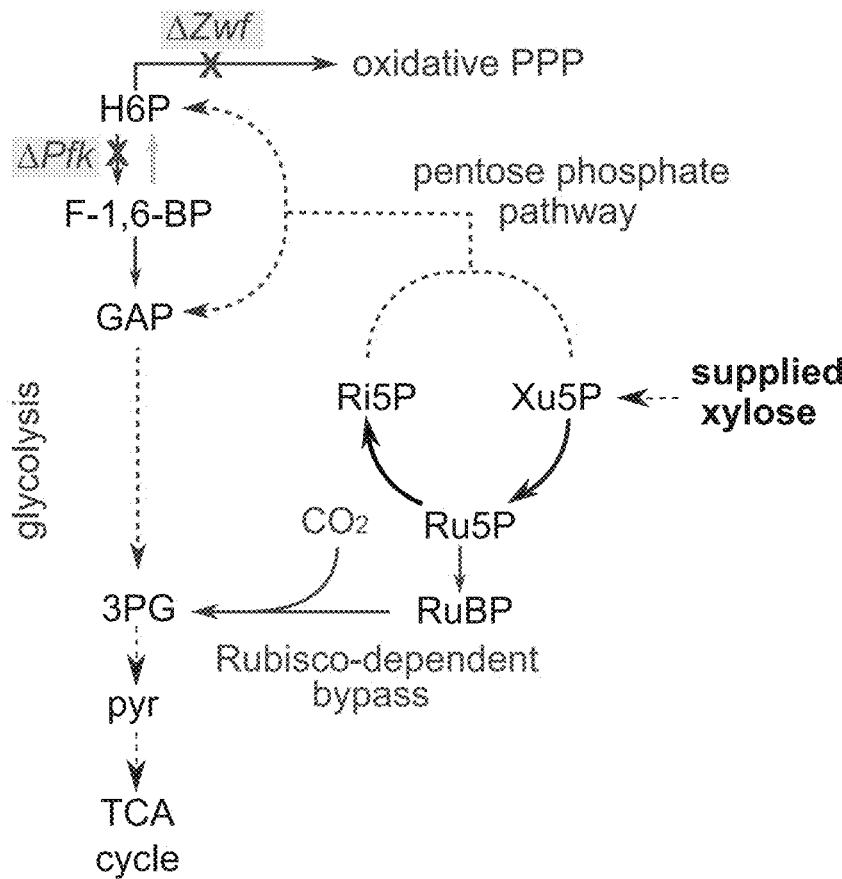

FIG. 6D external carbon source: xylose

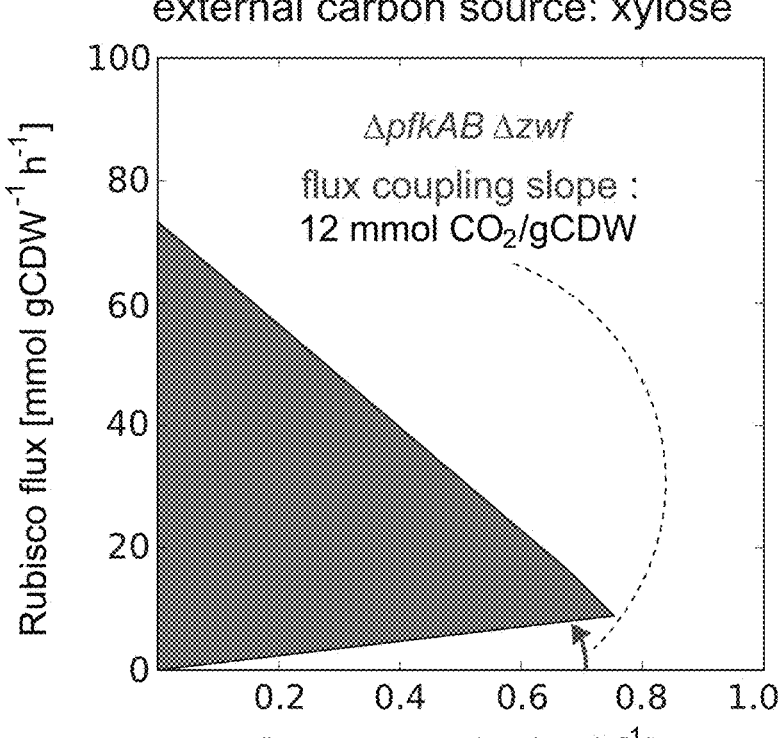

$\Delta pfkAB\ \Delta zwf$
flux coupling slope :
12 mmol $CO_2$/gCDW

Rubisco flux [mmol gCDW$^{-1}$ h$^{-1}$]

Biomass production [h$^{-1}$]

FIG. 6E experimental validation

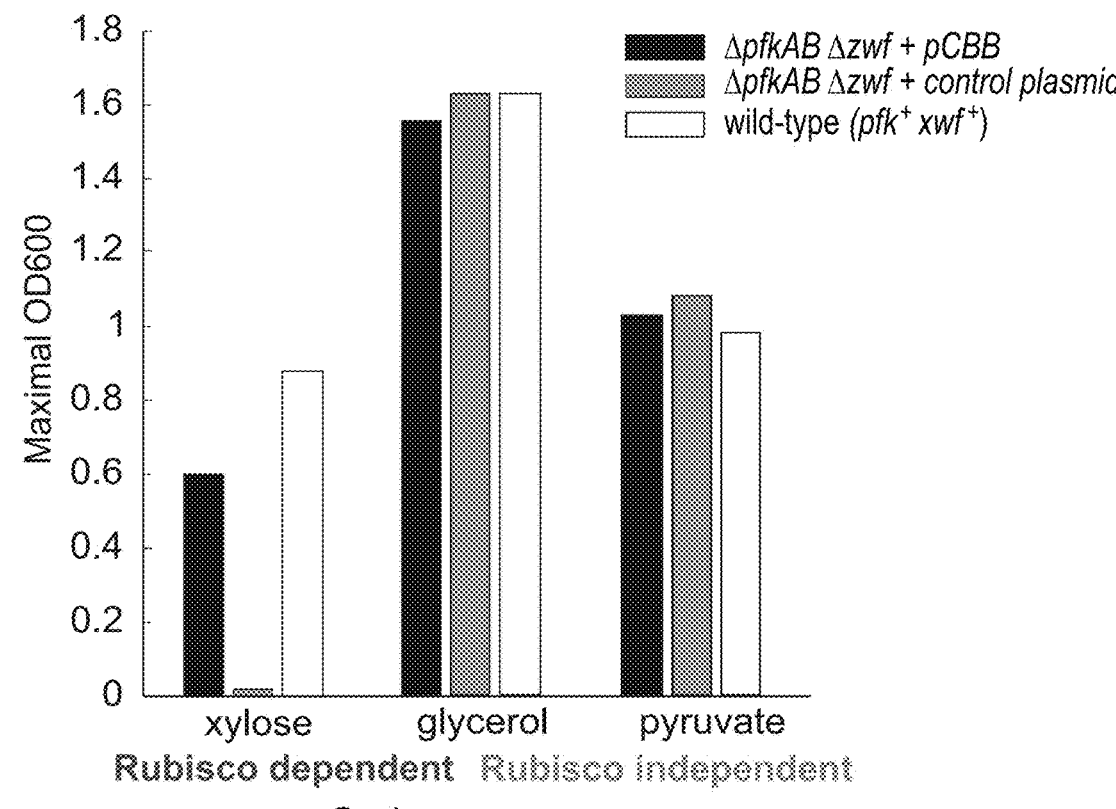

Maximal OD600

- ■ $\Delta pfkAB\ \Delta zwf$ + pCBB
- ▦ $\Delta pfkAB\ \Delta zwf$ + control plasmid
- □ wild-type (pfk$^+$ xwf$^+$)

xylose  glycerol  pyruvate

Rubisco dependent  Rubisco independent

Carbon source

FIG. 8B     $^{12}CO_2$+$^{13}$C-formate
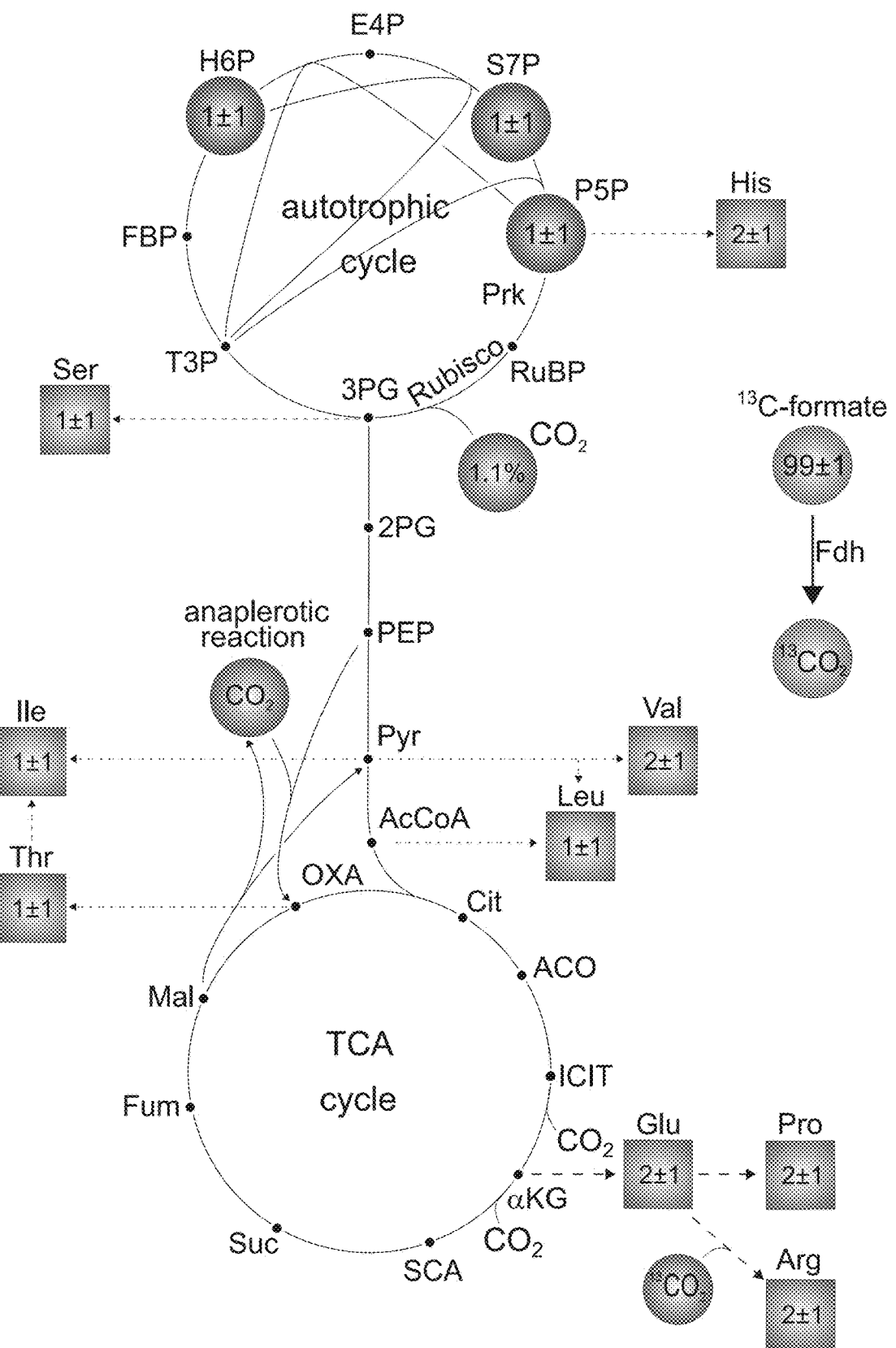

$$\%^{13}CO_2 = \%^{13}C\text{-}Arg*6 - \%^{13}C\text{-}Glu*5 = 87.0\%*6 - 86.4\%*5 = 90\%$$

$$\text{normalized } ^{13}C \% \text{ of metabolite carbon} = \frac{\text{Raw measured }^{13}C \% \text{ of metabolite carbon}}{\text{computed } \%^{13}CO_2 \text{ out of total } CO_2}$$

e.g.     $\dfrac{90\% \text{ of valine carbon is }^{13}C}{90\% \text{ of } CO_2 \text{ carbon is }^{13}C}$     $\dfrac{100\% \text{ of valine carbon is}}{^{13}C \text{ after normaliztion}}$

ENGINEERED AUTOTROPHIC BACTERIA FOR $CO_2$ CONVERSION TO ORGANIC MATERIALS

RELATED APPLICATIONS

This application is a National Phase of PCT Patent Application No. PCT/IL2020/051109 having International filing date of Oct. 22, 2020, which claims the benefit of priority under 35 USC § 119(e) of U.S. Patent Application No. 62/928,385 filed on Oct. 31, 2019. The contents of the above applications are all incorporated by reference as if fully set forth herein in their entirety.

SEQUENCE LISTING STATEMENT

The ASCII file, entitled 91660SequenceListing.txt, created on Apr. 12, 2022, comprising 19,278 bytes, submitted concurrently with the filing of this application is incorporated herein by reference.

FIELD AND BACKGROUND OF THE INVENTION

The present invention, in some embodiments thereof, relates to genetically modified bacteria and more specifically to bacteria which have been genetically modified such that they are capable of converting carbon dioxide to organic materials.

Autotrophic organisms, which generate biomass by fixing inorganic carbon into organic compounds, are the main gateway between the inorganic and living worlds. They dominate the biomass on Earth, supplying all of our food and most of our fuel. A better understanding of the principles of autotrophic growth and methods to enhance it are thus critical on the path to sustainability. By constructing synthetic autotrophic organisms, we could learn what the main constraints are on natural autotrophs and how to improve their central metabolic pathways. Thus, a grand challenge in synthetic biology is to engineer autotrophy within a model heterotrophic organism.

To enable a complete transition to autotrophy, the host must (1) operate $CO_2$ fixation machinery in a pathway where the carbon input is comprised solely of $CO_2$, while the outputs are organic molecules that enter central carbon metabolism and supply all 12 essential biomass precursors of the cell; (2) express enzymatic machinery to obtain reducing power, either by harvesting non-chemical energy (light, electricity, etc.) or by oxidizing a reduced chemical compound that does not serve as a carbon source; (3) regulate and coordinate the energy-harvesting and $CO_2$-fixation pathways so that they together support steady-state growth with $CO_2$ as the sole source of carbon. Previous attempts (Mattozzi et al., 2013; Antonovsky et al., 2016; von Borzyskowski et al., 2018) to establish autocatalytic $CO_2$ fixation cycles in model heterotrophs required the addition of multi-carbon organic compounds, which served, at least partially, as a carbon source, in order to achieve stable growth. Specifically, the metabolic design in Antonovsky et al., 2016 and Herz et al., 2017 was such that $CO_2$ was the source of only a third of the cellular biomass carbon, with the rest supplied by an organic acid that served also as the reducing power and energy source. Therefore, the engineering of a heterotrophic organism to supply all its biomass components from inorganic carbon is still a standing challenge.

Background art includes WO2014/020599, WO2015/087327 and WO2015/177800.

SUMMARY OF THE INVENTION

According to an aspect of the present invention there is provided a recombinant bacteria which is genetically modified to express formate dehydrogenase (FDH), phosphoribulokinase (prk) and Ribulose-Bisphosphate Carboxylase/oxygenase (RuBisCo).

According to an aspect of the present invention there is provided a cell culture comprising a medium and the recombinant bacteria described herein, wherein the medium comprises formate.

According to an aspect of the present invention there is provided a method of generating an autotrophic bacteria comprising:

(a) obtaining a bacteria which expresses a recombinant formate dehydrogenase (FDH), phosphoribulokinase (prk) and Ribulose-Bisphosphate Carboxylase/oxygenase (RuBisCo), the bacteria being modified to down-regulate expression of zwf, pfkA and pfkB;

(b) culturing the bacteria in a medium comprising a pentose or hexose sugar; and subsequently (c) reducing the amount of the pentose or hexose sugar in the medium and increasing the amount of formate in the medium.

According to embodiments of the present invention the recombinant bacteria is further genetically modified to express carbonic anhydrase (CA).

According to embodiments of the present invention the bacteria is modified so as to down-regulate the amount or activity of 6-phosphate-1-dehydrogenase (zwf), phosphofructokinase A (pfkA) and phosphofructokinase B (pfkB).

According to embodiments of the present invention the bacteria is modified so as to alter the amount or activity of glucosephosphate isomerase (pgi).

According to embodiments of the present invention the bacteria is modified so as to alter the amount or the activity of phosphoribosylpyrophosphate synthase (prs).

According to embodiments of the present invention the bacteria is modified so as to alter the amount or the activity of uridylate kinase (pyrH).

According to embodiments of the present invention the bacteria is modified so as to alter the amount or activity of 3-deoxy-D-arabino-heptulosonate-7-phosphate synthase (aroH) or enolase (eno).

According to embodiments of the present invention the bacteria has a mutation in at least one of the genes selected from the group consisting of RNA polymerase, beta subunit (rpoB), mal regulon transcriptional activator (malI) and poly(A) polymerase (pcnB).

According to embodiments of the present invention, the recombinant bacteria has a mutation in each of the genes RNA polymerase, beta subunit (rpoB), mal regulon transcriptional activator (malI), poly(A) polymerase (pcnB) and glucosephosphate isomerase (pgi).

According to embodiments of the present invention, the recombinant bacteria has a mutation in at least one additional gene which is set forth in any one of Tables 4-9.

According to embodiments of the present invention, the bacteria is an *E. coli*.

According to embodiments of the present invention, the bacteria is an autotroph.

According to embodiments of the present invention, the bacteria is not, in its native state, capable of biosynthesizing metabolites by utilizing $CO_2$ as a sole carbon source.

According to embodiments of the present invention, the bacteria is not a cyanobacteria.

According to embodiments of the present invention, the cell culture is devoid of an additional organic carbon source.

According to embodiments of the present invention, the bacteria express recombinant carbonic anhydrase.

According to embodiments of the present invention, the bacteria are modified so as to down-regulate amount or activity of pgi.

According to embodiments of the present invention, the bacteria are modified so as to alter the amount or activity of prs.

According to embodiments of the present invention, the bacteria are modified so as to alter the amount or the activity of uridylate kinase (pyrH).

According to embodiments of the present invention, the bacteria are modified so as to alter the amount or activity of aroH or eno.

According to embodiments of the present invention, the bacteria have a mutation in at least one of genes selected from the group consisting of rpoB, malT and pcnB.

According to embodiments of the present invention, the bacteria have a mutation in each of the genes rpoB, malT, pcnB and pgi.

According to embodiments of the present invention, the bacteria have a mutation in at least one additional gene which is set forth in any one of Tables 4-9.

According to embodiments of the present invention, the bacteria are E. coli.

According to embodiments of the present invention, the bacteria are not, in its native state, capable of biosynthesizing metabolites by utilizing $CO_2$ solely as a carbon source.

According to embodiments of the present invention, the bacteria are not a cyanobacteria.

According to embodiments of the present invention, the pentose sugar is xylose.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL
VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 1:
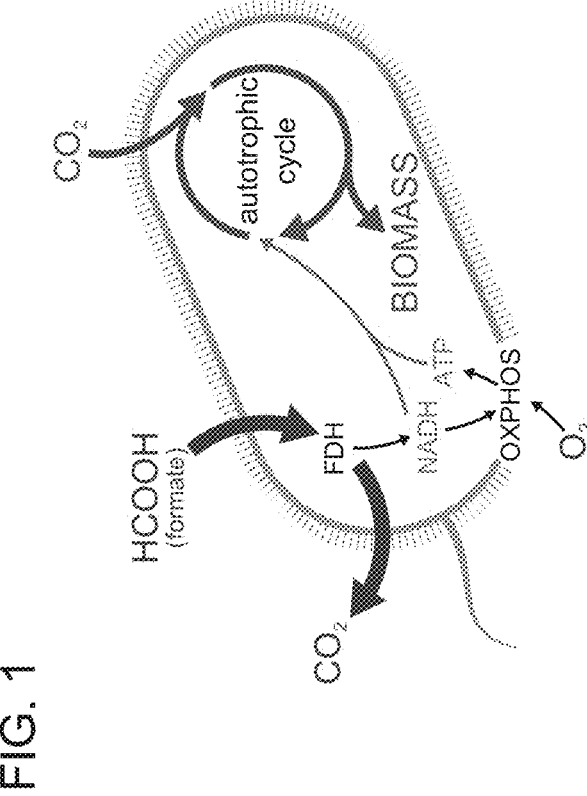

In the drawings:

FIG. 1. Schematic representation of the engineered synthetic chemo-autotrophic E. coli. $CO_2$ (green) is the only carbon source for all the generated biomass. The fixation of $CO_2$ occurs via an autotrophic carbon assimilation cycle. Formate is oxidized by a recombinant formate dehydrogenase (FDH) to produce $CO_2$ (brown) and NADH. NADH provides the reducing power to drive carbon fixation and serves as the substrate for ATP generation via oxidative phosphorylation (OXPHOS in black). The formate oxidation arrow is thicker than the $CO_2$ fixation arrow, thus indicating a net $CO_2$ emission even under autotrophic conditions.

Figure 2A:
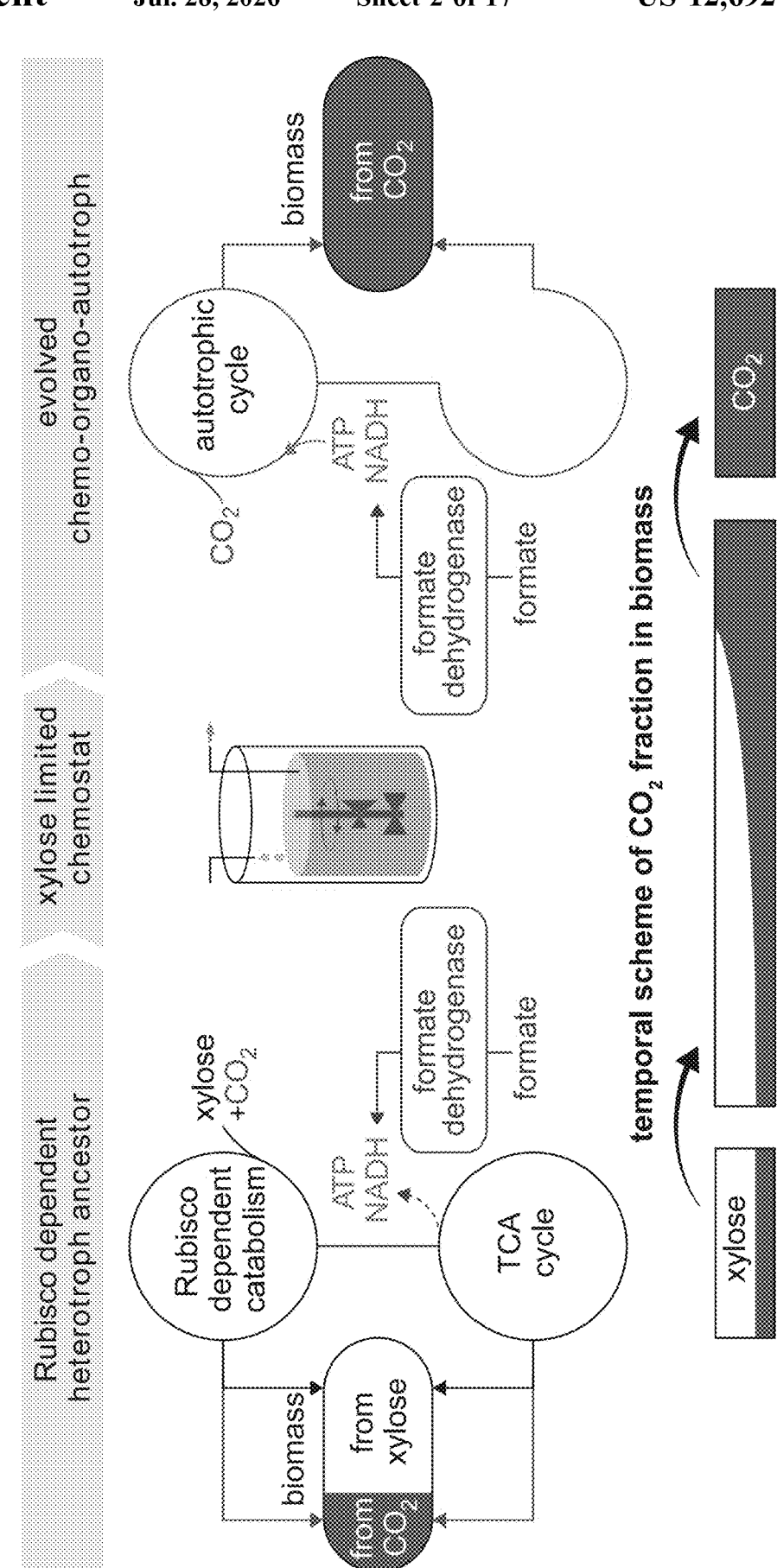
Figure 2B:
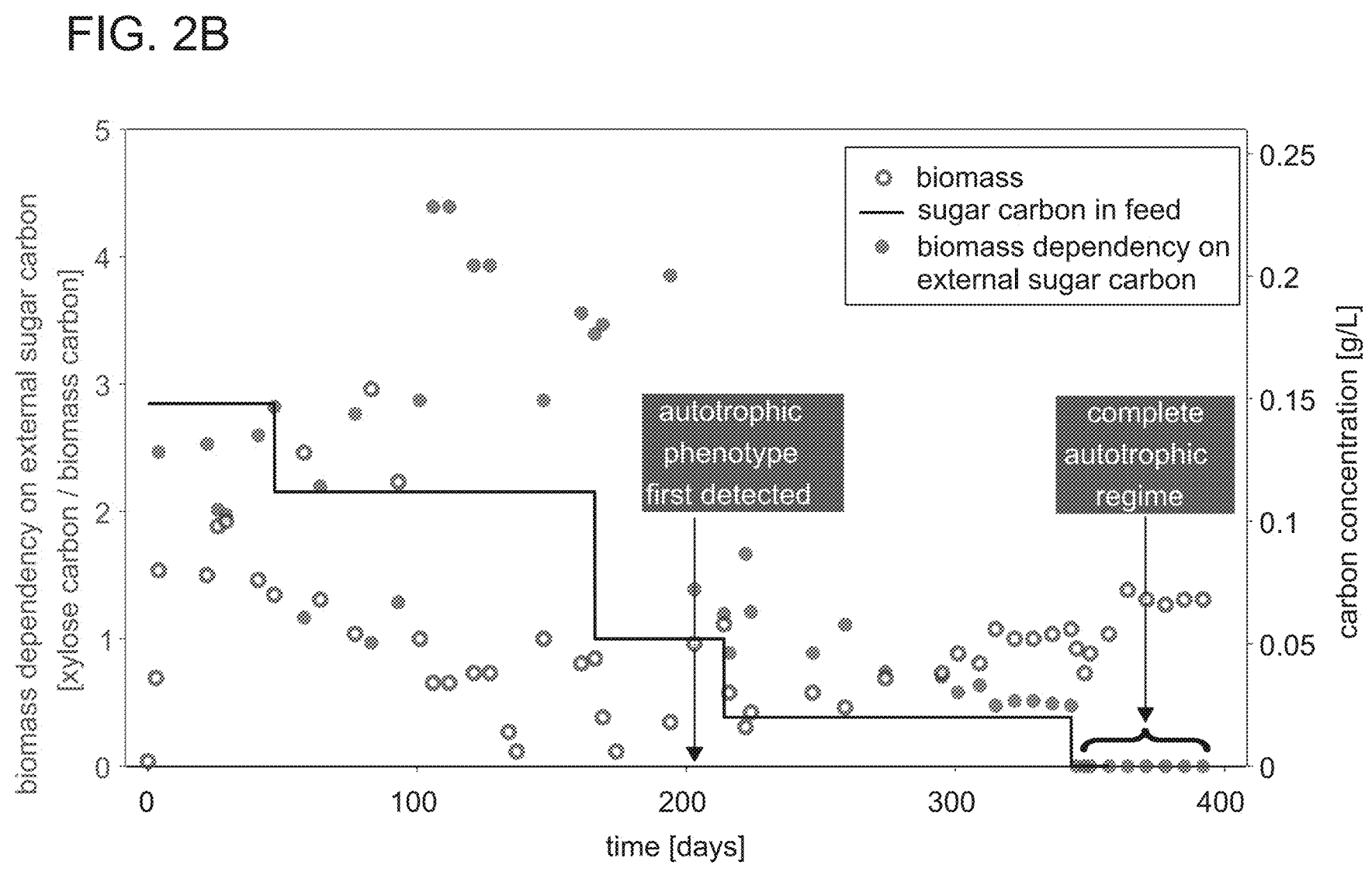
Figure 2C:
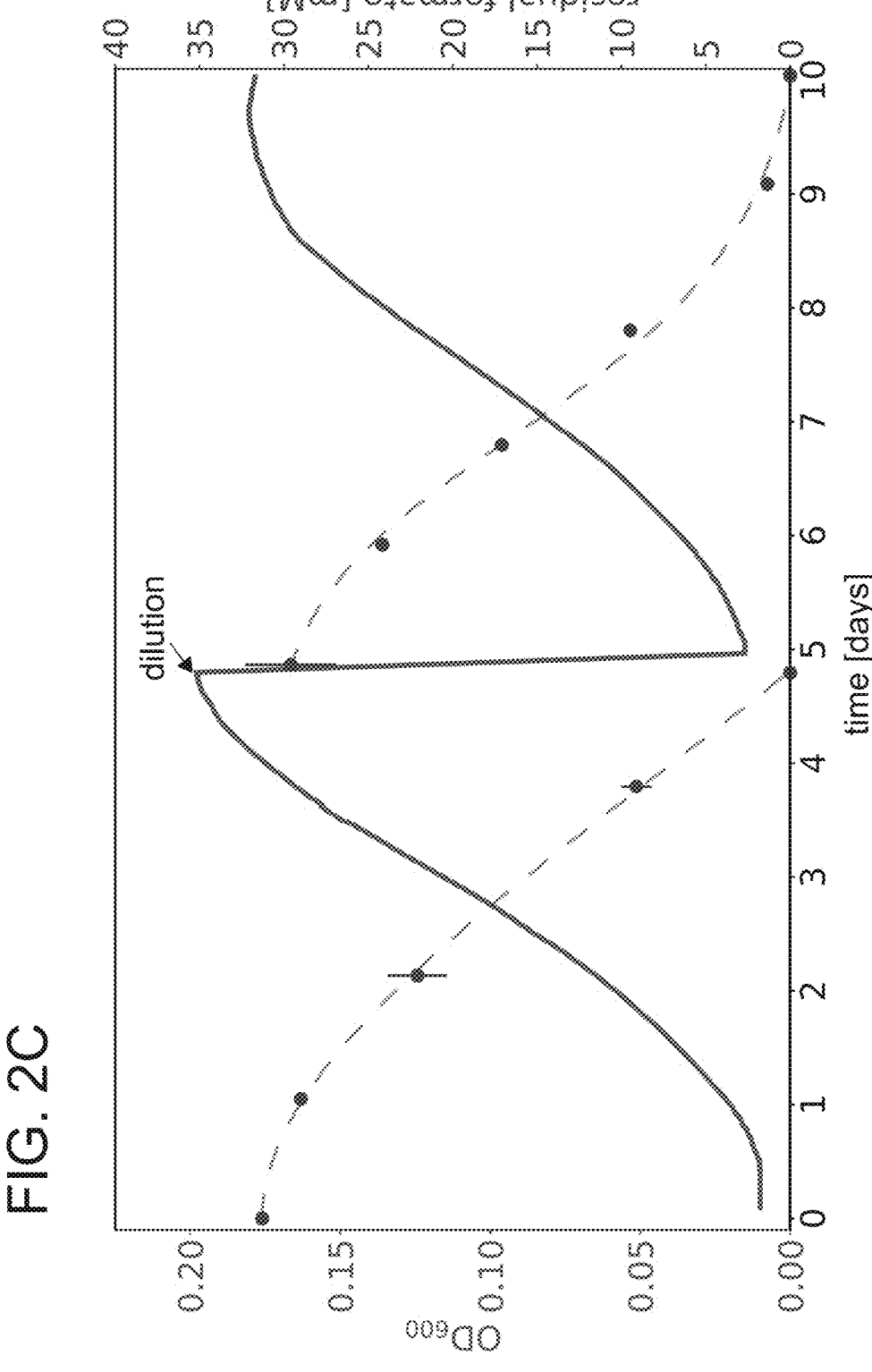

FIGS. 2A-C. Tailored evolutionary strategy from a rationally designed engineered E. coli strain towards an evolved chemo-autotroph. (A) The parental strain for the evolution (left) harbouring knockouts of the pfkAB and zwf genes, and overexpressing Rubisco, Prk, CA and FDH, assimilates $CO_2$ to enable xylose catabolism via the Rubisco-Prk shunt (see also FIGS. 5A-C) but is unable to grow in autotrophic conditions. Upon xylose starvation in a xylose-limited chemostat with an excess of formate and $CO_2$, the cells are under a strong selection pressure to use $CO_2$ as the only carbon source, while using formate oxidation by FDH as the energy source. Evolved clones with a fully autotrophic phenotype (right) and a maximal growth rate in the absence of xylose higher than the dilution rate of the chemostat are predicted to have a fitness advantage over xylose-dependent clones and can take over the population. (B) The ancestral strain was inoculated into a xylose-limited chemostat with a dilution rate of $0.02 \text{ h}^{-1}$. The concentration of the externally supplied sugar D-xylose in the feed media (black line) was decreased several times throughout the experiment. The biomass dependency on the externally supplied sugar (green dots) decreased starting at day 120, from a value of $\approx 15$ xylose carbons/biomass carbon to zero following day 340 ($\approx 250$ chemostat generations). Starting from day 203 ($\approx 150$ chemostat generations) of the experiment and onwards, we observed that samples taken from the chemostat could grow on minimal media supplemented only with formate and elevated $CO_2$. For time points where the culture was not in steady chemostat mode (as described in the methods), the biomass dependency measure is not shown. (C) Repeated growth of the isolated evolved clone in liquid M9 minimal media with 30 mM sodium formate and sparged with a gas mixture of 10% $CO_2$, 90% air. The doubling time of the evolved cells at the given conditions is 18±4 hours. Growth was carried out in DASGIP fermenters (150 ml working volume). Residual formate concentrations are represented by brown circles (see also FIG. 7).

Figure 3A:
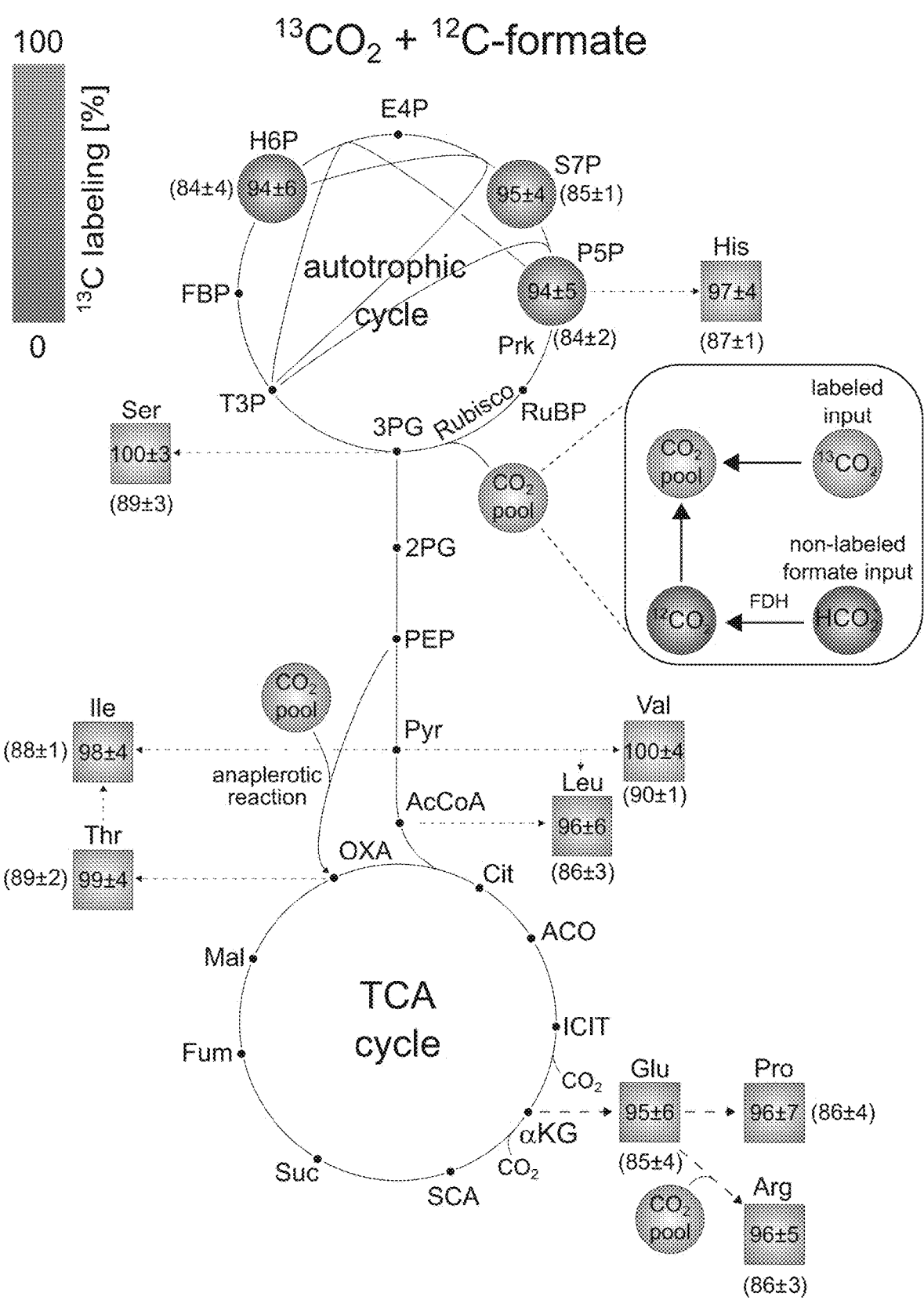
Figure 3B:
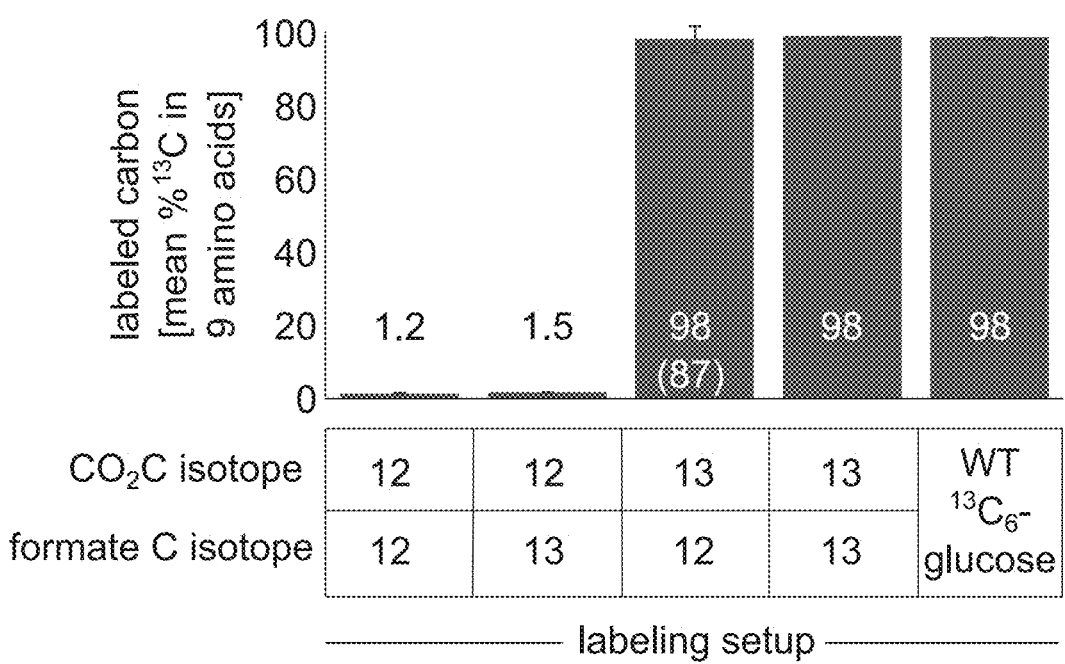

FIGS. 3A-B. Isotopic labeling experiments using $^{13}$C show that all biomass components are generated from $CO_2$ as the sole carbon source. (A) Values are based on LC-MS analysis of stable amino acids and sugar-phosphates (see methods). The fractional contribution of [13]$CO_2$ to various protein-bound amino acids and sugar-phosphates of evolved cells grown on [13]$CO_2$ and naturally labeled formate showed almost full $^{13}$C labeling of the biosynthesized amino acids. The numbers reported are the $^{13}$C fraction of each metabolite, taking into account the effective [13]$CO_2$ fraction out of the total inorganic carbon (which decreases due to unlabeled formate oxidation to $CO_2$). The numbers in parentheses are the uncorrected measured values of the $^{13}$C fraction of the metabolites. (Data are presented as mean ±S.D.; n=5). (B) The average $^{13}$C fraction of nine analyzed amino acids of the evolved clone grown in different experimental setups. Experiments with [13]$CO_2$ as the substrate were carried in air-tight (i.e., "closed") growth vessels. The bar with the parenthesis represents the mean value after correction for the effective labeled fraction of $CO_2$ in the experiment given the "pollution" with $CO_2$ generated via formate oxidation and retention in the closed growth vessel. The value in the parenthesis is the measured one, and outside the parentheses is presented the corrected value. As a positive control for maximal biomass $^{13}$C labeling, we grew wild-type E. coli in M9 minimal media supplemented with $^{13}C_6$-Glucose (far right). Error bars denote standard deviation. See also FIGS. 8A-B and 9A-B.

Figure 4:
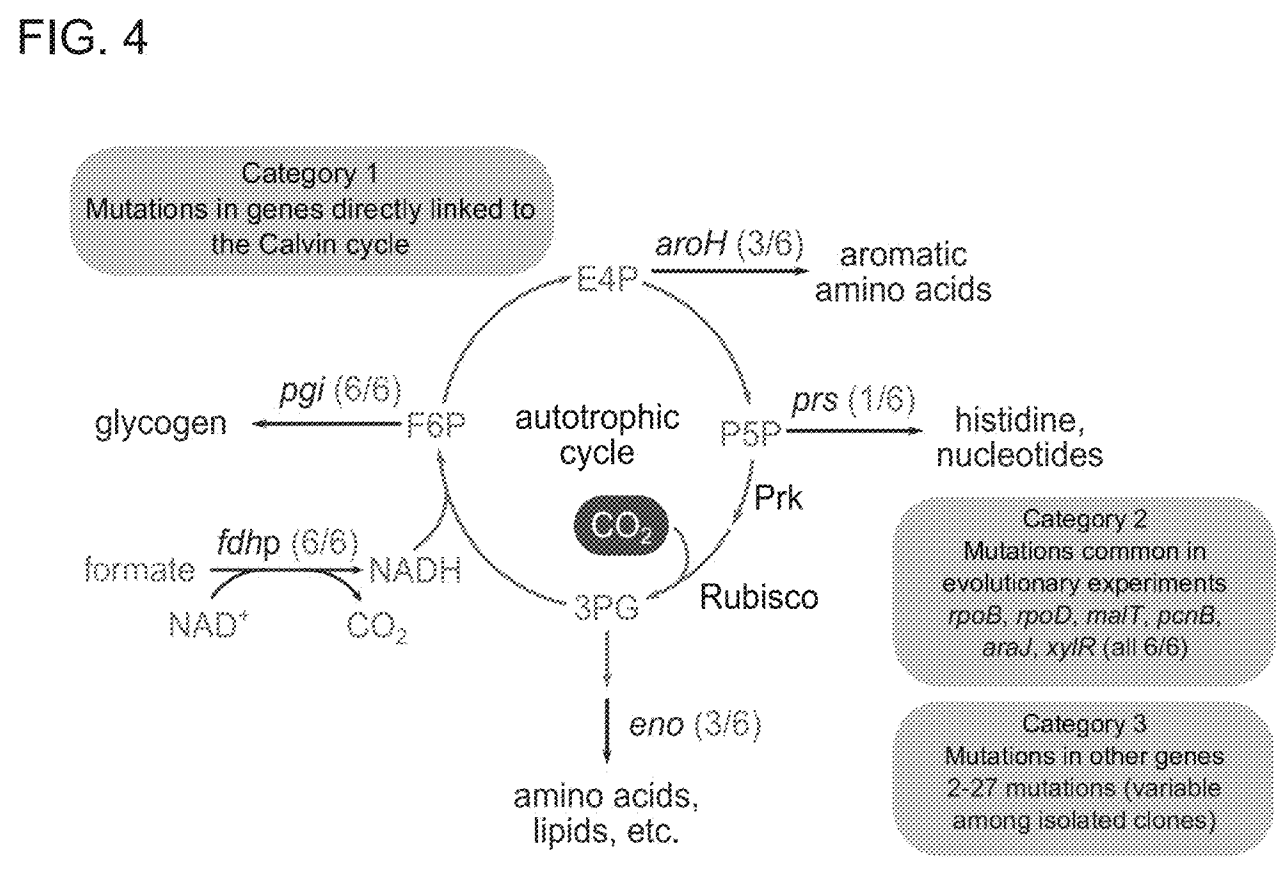

FIG. 4. The genetic basis for adaptation to autotrophy. The names of the mutated genes appear in red. The parentheses indicate the number of isolated clones in which the mutation appeared. As discussed in the main text, mutations observed across isolated clones can be divided into three broad groups. The first category includes mutations in genes with a direct metabolic link to the Calvin cycle, mostly flux branch points. The second category includes genes which are generic mutations common in other adaptive laboratory evolution experiments conducted with *E. coli*. The last category includes genes with uncharacterized role. Acronyms: E4P—erythrose-4-phosphate; P5P—pentose-5-phosphates; F6P—fructose-6-phosphate; 3PG—glycerate-3-phosphate. See Tables 4-9.

Figure 5A:
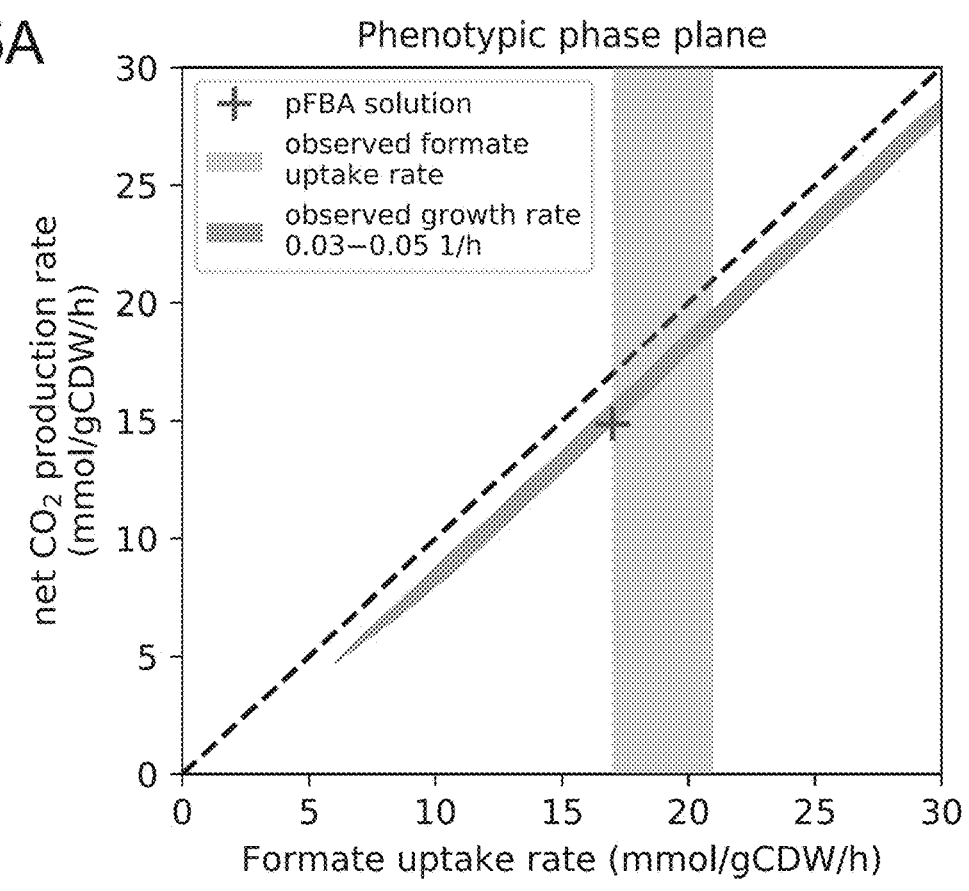
Figure 5B:
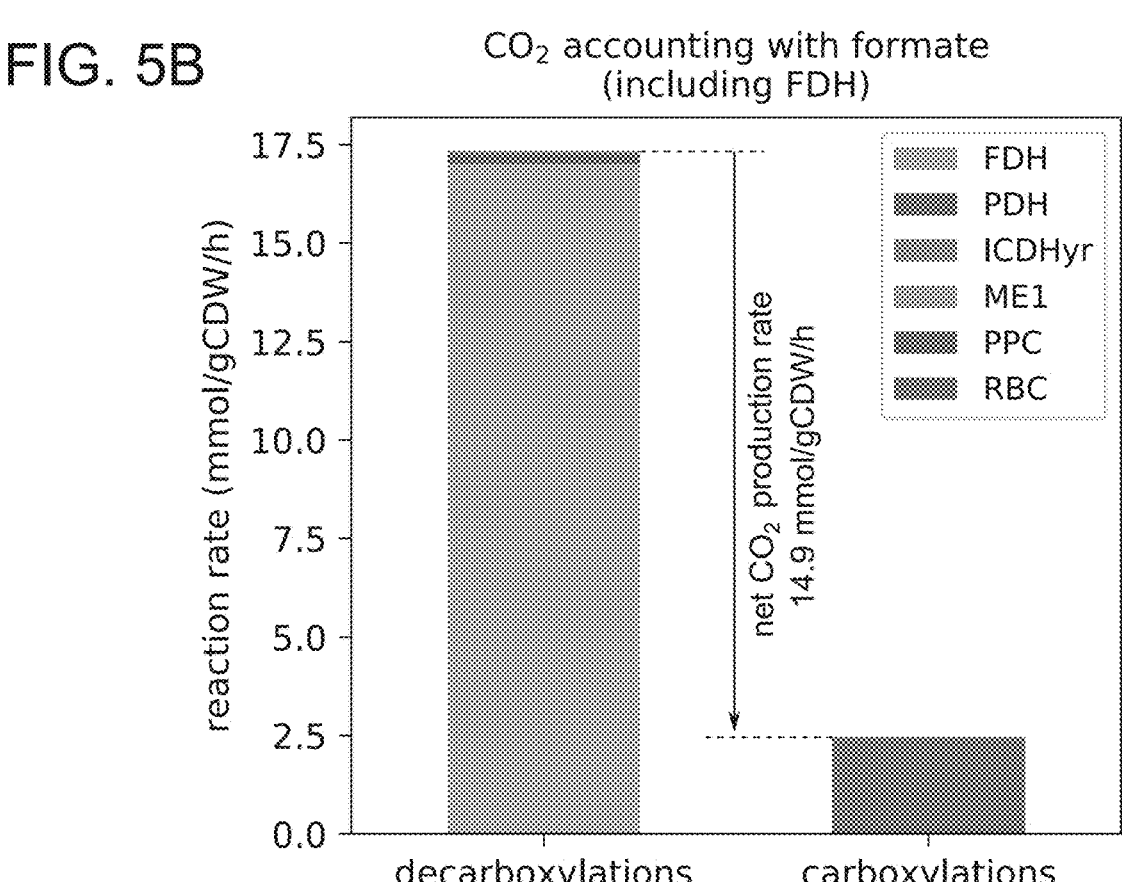
Figure 5C:
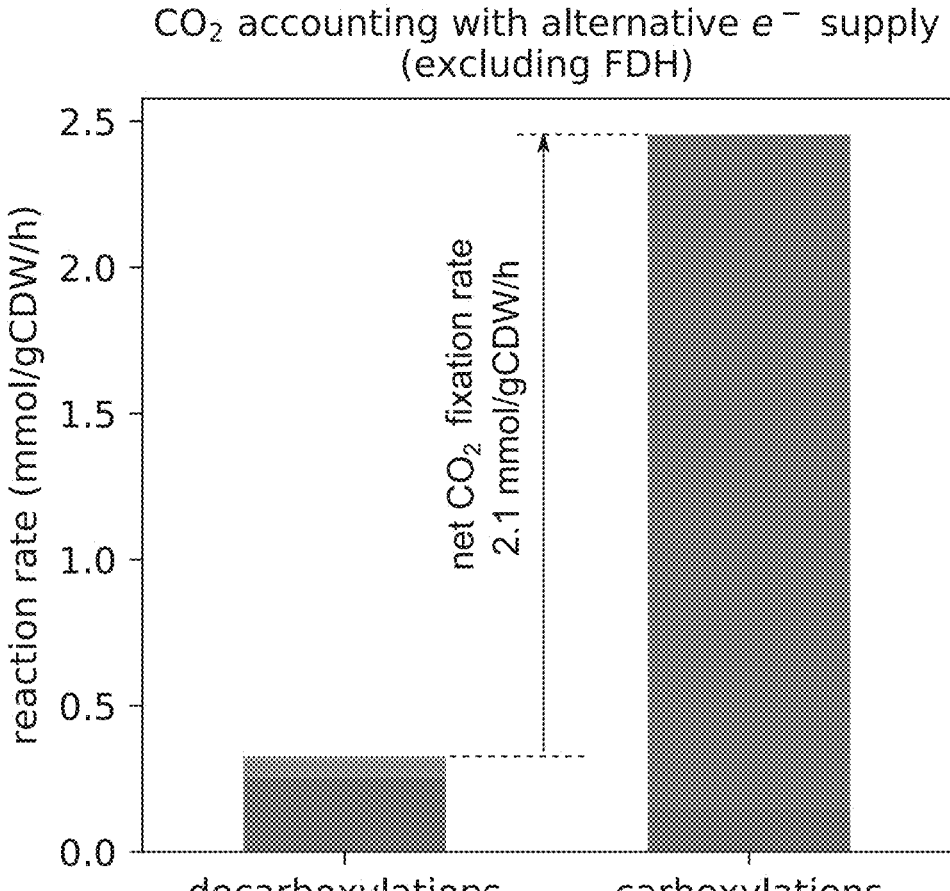

FIGS. 5A-C. Flux balance analysis of the autotrophic *E. coli*. (A) Phenotypic phase plane showing the feasible space given the measured growth rate (0.04±0.01 h$^{-1}$) of the evolved strain (blue line). There is strong coupling between the formate uptake and the net $CO_2$ production rate since formate can only be metabolised via FDH in our model. In reality, formate can be used for a relatively small flux of C1-related biosynthesis and these reactions are not part of the core model. However, at the measured growth rate, these fluxes are negligible compared to the FDH rate. The yellow shading indicates our measured value for the formate uptake rate (19±2 mmol/gCDW/h). The blue cross indicates the flux balance analysis solution with the minimal total sum of fluxes (also known as pFBA). (B) Stacked bar plot showing the fluxes of all carboxylation and decarboxylation reactions, for the pFBA solution. FDH is by far the most significant decarboxylator, and rubisco is the major carboxylating reaction. (C) Same as B, except that we assume an alternative source for electrons which is $CO_2$ neutral (note that the scale of the y-axis is different). For example, if formate is produced electrochemically, its contribution to the net $CO_2$ would cancel out.

FIGS. 6A-E. Metabolic configuration for mixotrophic Rubisco-dependent growth. (A) Metabolic depiction of native route of xylose metabolism in *E. coli* via the pentose phosphate pathway into glycolysis. (B) Knockout of the glycolytic phosphofructokinase (PfK) reaction and glucose-6-phosphate dehydrogenase (Zwf) reaction eliminate the possibility to shunt hexose-phosphates to any oxidative pathways and lead to their accumulation and arrest of growth. (C) Growth of the knockout strain could be rescued upon shunting excess pentose-phosphates via the carbon fixation branch (Prk+Rubisco) into glycolysis. (D) Computational prediction regarding the coupling between carboxylation flux through Rubisco (y axis) and growth (x axis) of the metabolic configuration depicted in panel C. (E) experimental validation of the ΔpfkABΔzwf metabolic configuration: dependency on the expression of the carbon fixation branch is found only when xylose serves as the single organic carbon.

Figure 7:
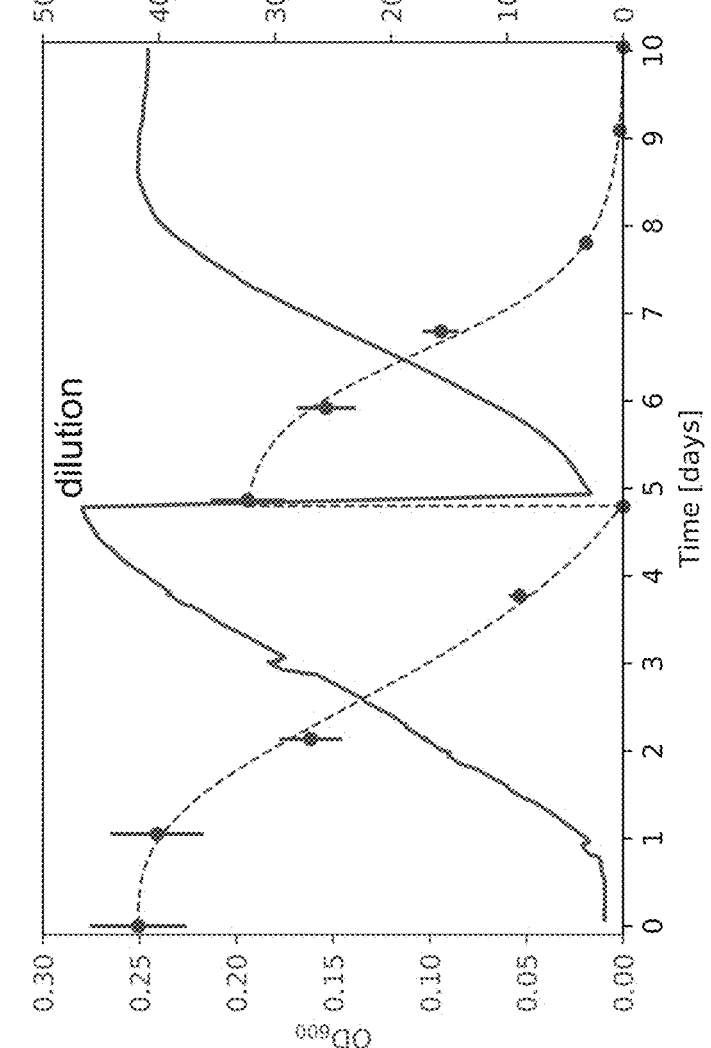

FIG. 7. Growth curve in minimal media with 35 mM sodium formate. Repeated growth of the isolated evolved clone in liquid M9 minimal media with 35 mM sodium formate and sparging with a gas mixture of 10% $CO_2$, 90% Air. The doubling time of the evolved cells at the given conditions is 18±4 hours. The residual concentrations of formate are shown in brown.

Figure 8A:
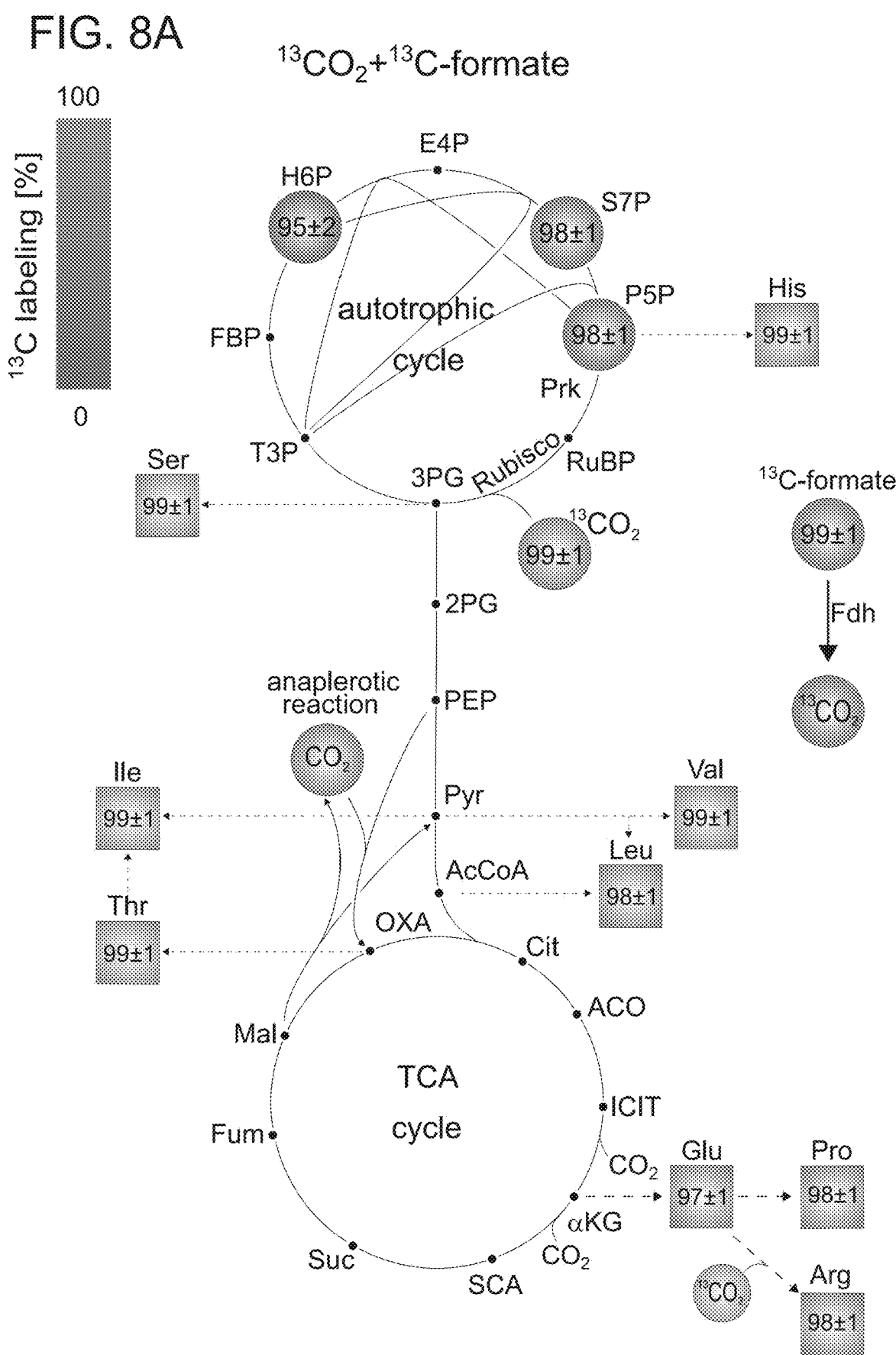

FIGS. 8A-B. Amino acid $^{13}C$ labeling profile in additional labeling experiments. (A) The $^{13}C$ fraction of various protein-bound amino acids and sugar-phosphates is close to 100% when the evolved cells were grown on $^{13}CO_2$ and labeled $^{13}C$ formate. The experiment was carried out in closed vessels (n=3; ±S.D.). (B) The fractional contribution of $^{13}C$ formate to various protein-bound amino acids and sugar-phosphates of evolved cells grown on $^{12}CO_2$ and labeled $^{13}C$-formate showed minute $^{13}C$ labeling of the sugar-phosphates and biosynthesized amino acids. The experiment was carried out in gas permeable vessels (n=3; ±S.D.).

Figure 9A:
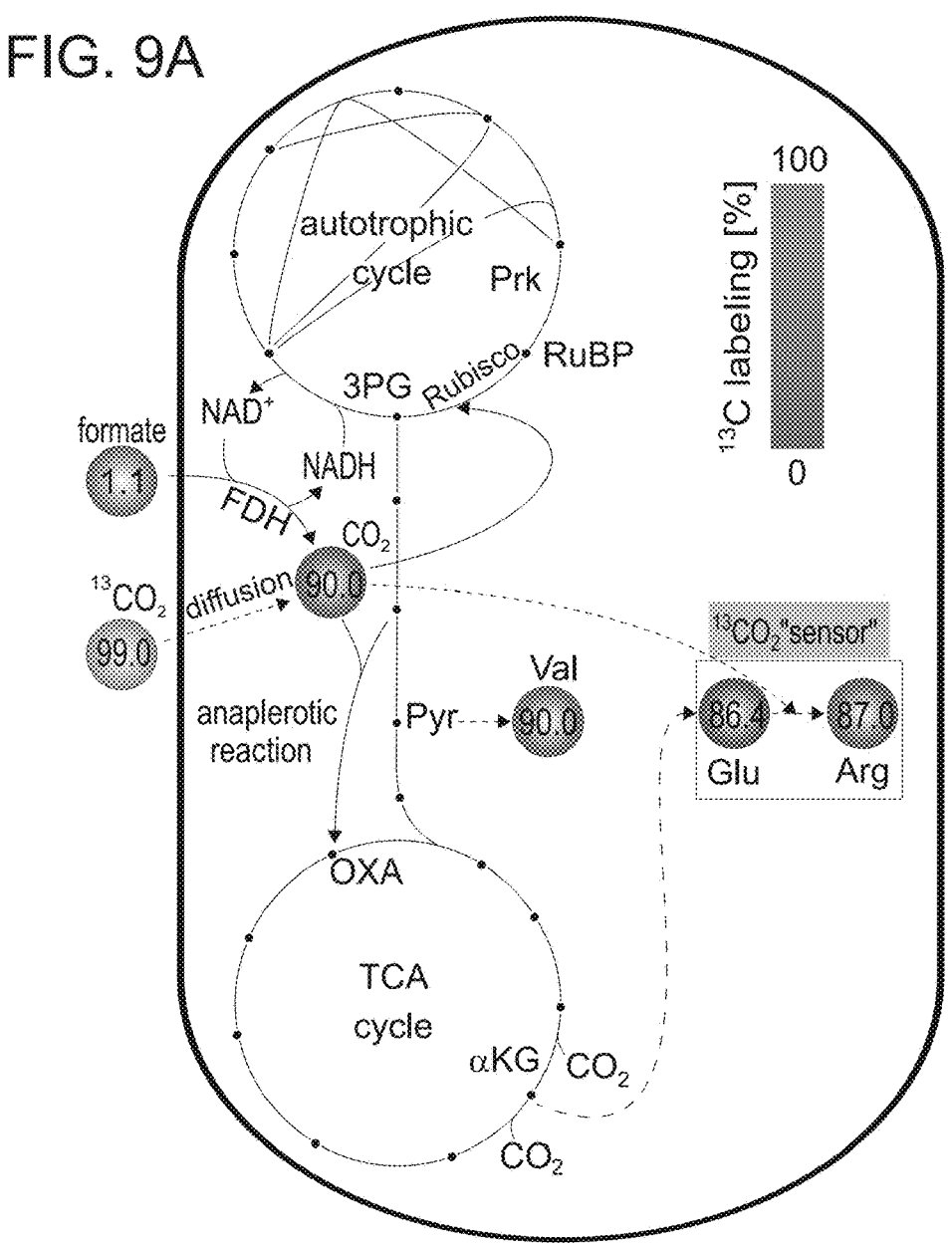
Figure 9B:
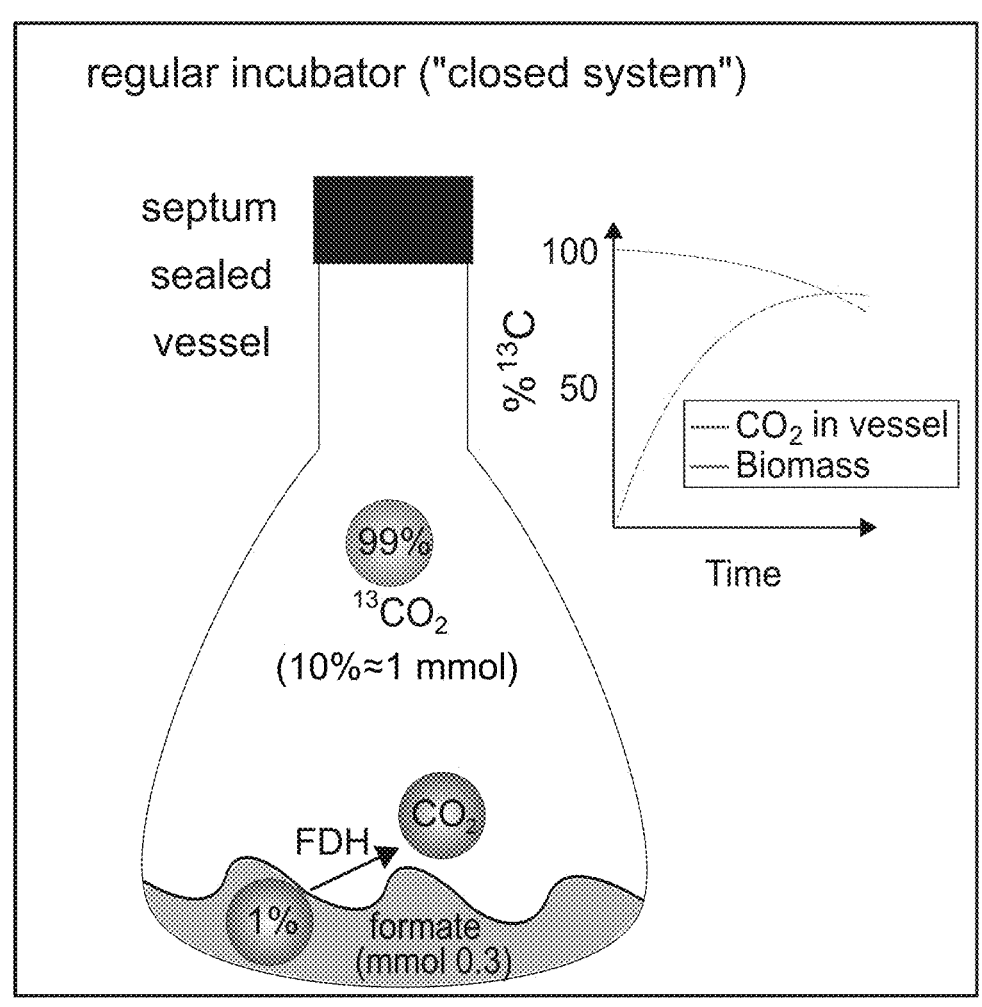

FIGS. 9A-B. Calculating the effective $^{13}CO_2$ fraction during the experiments, related to FIGS. 3A-B. (A) The weighted average of the effective isotopic composition of $CO_2$ during the experiment can be computed from the measured labeled fractions of glutamate and arginine, which we define as a $^{13}CO_2$ "sensor". The bottom box describes the calculation method and its implementation in the subsequent normalization of the raw labeling measurements of various metabolites (e.g., valine). (B) The experimental setup of isotopic biomass labeling with $^{13}CO_2$ consists of a septum-sealed 250 ml growth flask and 10 ml of minimal M9 media with 30 mM naturally labeled sodium formate. In total, the vessel contains 0.3 mmol formate and ≈1 mmol of $^{13}CO_2$ at the beginning of the experiment. The latter is flushed into the headspace via a thin needle, which is removed at the end of the flushing procedure. The initial inoculum of cells is also naturally labeled. As the cells grow and oxidize the formate to obtain energy, the isotopic composition of inorganic carbon within the vessel changes as depicted in the plot (blue line). The isotopic dynamics of the biomass carbon during autotrophic growth is depicted by the red line.

DESCRIPTION OF SPECIFIC EMBODIMENTS OF THE INVENTION

The present invention, in some embodiments thereof, relates to genetically modified bacteria and more specifically to bacteria which have been genetically modified such that they are capable of converting carbon dioxide to organic materials.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The living world is largely divided into autotrophs that convert $CO_2$ into biomass and heterotrophs that consume organic compounds. In spite of widespread interest in renewable energy storage and more sustainable food production, the engineering of industrially-relevant heterotrophic model organisms to use $CO_2$ as their sole carbon source has so far remained an unmet challenge.

The present inventors have now constructed and evolved *Escherichia coli* to produce all its biomass carbon from $CO_2$. Reducing power and energy, but not carbon, is supplied via the one-carbon molecule formate, which can be produced electrochemically. Rubisco and phosphoribulokinase were co-expressed with formate dehydrogenase to enable $CO_2$ fixation and reduction via the Calvin-Benson-Bassham cycle. Autotrophic growth was achieved following several months of continuous laboratory evolution in a chemostat under intensifying organic carbon limitation and confirmed via isotopic labeling (FIGS. 3A-B). Sequencing analysis uncovered particular genes that were mutated in each of the clones (FIG. 4).

Thus, according to a first aspect of the present invention, there is provided a recombinant bacteria which is genetically modified to express formate dehydrogenase (FDH), phosphoribulokinase (prk) and Ribulose-Bisphosphate Carboxylase (RuBisCo).

Bacteria of this aspect of the present invention may be gram positive or gram negative. Examples of bacteria which are contemplated by the present invention include, but are not limited to *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus,* and *Zymomonas.*

Contemplated bacteria may be those which are useful in the food industry. For example lactic Acid Bacteria (LAB) play an essential role in the preservation, taste and texture of cheese, yogurt, sausage, sauerkraut and a large variety of traditional indigenous fermented foods.

According to a particular embodiment, the bacteria is of the *Escherichia* genus (e.g., *E. Coli*).

According to embodiments of the present invention, the bacteria is not (in its native state), capable of biosynthesizing metabolites by utilizing $CO_2$ solely as a carbon source. Thus, for example, the bacteria are not cyanobacteria.

The bacteria of this aspect of the present invention are genetically modified to express two enzymes of the Calvin-Benson-Bassham (CBB) Cycle—namely phosphoribulokinase (PRK; EC 2.7.1.19) and ribulose-1,5-bisphosphate carboxylase/oxygenase (RuBisCO; EC 4.1.1.39). In addition, the bacteria of this aspect of the present invention are genetically modified to express formate dehydrogenase (EC 1.17.1.9).

Optionally, the bacteria of this aspect of the present invention is genetically modified to also express carbonic anhydrase (EC 4.2.1.1).

In one embodiment, the enzyme which is expressed in the bacteria of the present invention is a homolog and/or comprises modifications including additions or deletions of specific amino acids to the sequence (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to the native amino acid sequence of the enzyme, as determined using BlastP software of the National Center of Biotechnology Information (NCBI) using default parameters). The homolog may also refer to an ortholog, a deletion, insertion, or substitution variant, including an amino acid substitution, thereof and biologically active polypeptide fragments thereof. The homolog typically retains the enzymatic activity of the native enzyme.

Thus RuBisCo may for example be a *Rhodospirillum rubrum* RuBisCo being encoded by a sequence as set forth in SEQ ID NO: 1 or having an amino acid sequence as set forth in SEQ ID NO: 5. The amino acid sequence may be at least 90% identical, at least 91% identical, at least 92% identical, at least 93% identical, at least 94% identical, at least 95% identical, at least 96% identical, at least 97% identical, at least 98% identical, at least 99% identical to SEQ ID NO: 5.

According to a particular embodiment, the RuBisCo is a plant-derived RuBisCo.

The PRK enzyme may be *Synechococcus* PRK being encoded by a sequence as set forth in SEQ ID NO: 2 or having an amino acid sequence as set forth in SEQ ID NO:

6. The amino acid sequence may be at least 90% identical, at least 91% identical, at least 92% identical, at least 93% identical, at least 94% identical, at least 95% identical, at least 96% identical, at least 97% identical, at least 98% identical, at least 99% identical to SEQ ID NO: 6. Alternatively, the RuBisCo and PRK may be expressed using an operon of the proteobacteria *Ralstonia eutropha,* which contains all the Calvin-Benson Cycle genes in tandem.

The carbonic anhydrase (EC 4.2.1.1) may be a *Rhodospirillum rubrum* carbonic anhydrase being encoded by a sequence as set forth in SEQ ID NO: 3 or having an amino acid sequence as set forth in SEQ ID NO: 7. The amino acid sequence may be at least 90% identical, at least 91% identical, at least 92% identical, at least 93% identical, at least 94% identical, at least 95% identical, at least 96% identical, at least 97% identical, at least 98% identical, at least 99% identical to SEQ ID NO: 7.

Expression of formate dehydrogenase (for example Gen-Bank AAB18330.2 and AAB18329.1, which is capable of oxidizing formate to carbon dioxide is also required. The formate dehydrogenase may be derived from the methytholotrophic bacterium *Pseudomonas* sp. 101 being encoded by a sequence as set forth in SEQ ID NO: 4 or having an amino acid sequence as set forth in SEQ ID NO: 8. The amino acid sequence may be at least 90% identical, at least 91% identical, at least 92% identical, at least 93% identical, at least 94% identical, at least 95% identical, at least 96% identical, at least 97% identical, at least 98% identical, at least 99% identical to SEQ ID NO: 8.

As used herein, "% identity" and "% homology" are used interchangeably and refer to the level of nucleic acid sequence identity or amino acid sequence identity between a first nucleic acid or amino acid sequence when aligned to a second nucleic acid or amino acid sequence using a sequence alignment program. When a position in the first and the second sequences is occupied by the same nucleic acid or amino acid (e.g., if a position in the first nucleic acid sequence and the second nucleic acid sequence is occupied by cytosine), then the first and the second sequences are homologous at that position. If the term "% homology" or "% identity" is used herein without an indication of whether such homology refers to nucleic acid sequence identity or amino acid sequence identity, the term shall be interpreted as referring to nucleic acid sequence identity.

In general, identity between two sequences is calculated from the number of matching or homologous positions shared by the two sequences over the total number of positions compared. In some embodiments, the first and the second sequences are aligned in a manner to maximize % homology. In some embodiments, % homology refers to the % identity over the shorter of two sequences. In some embodiments, the % homology for a nucleic acid sequence includes intronic and/or intergenic regions. Exemplary levels of % identity include, but are not limited to, 85, 86, 87, 88, 89, 90, 91, 92, 93, 94, 95, 96, 97, 98, 99% or more sequence identity between a first and a second sequence.

Exemplary sequence alignment programs that may be used to determine % homology between two sequences include, but are not limited to, the FASTA package (including rigorous (SSEARCH, LALIGN, GGSEARCH and GLSEARCH) and heuristic (FASTA, FASTX/Y, TFASTX/Y and FASTS/M/F) algorithms, the EMBOSS package (Needle, stretcher, water and matcher), the BLAST programs (including, but not limited to BLASTN, BLASTX, TBLASTX, BLASTP, TBLASTN), megablast and BLAT. In some embodiments, the sequence alignment program is BLASTN. For example, 95% homology refers to 95% sequence identity determined by BLASTN, by combining all non-overlapping alignment segments (BLAST HSPs), summing their numbers of identical matches and dividing this sum with the length of the shorter sequence.

In some embodiments, the sequence alignment program is a basic local alignment program, e.g., BLAST. In some embodiments, the sequence alignment program is a pairwise global alignment program. In some embodiments, the pairwise global alignment program is used for protein-protein alignments. In some embodiments, the pairwise global alignment program is Needle. In some embodiments, the sequence alignment program is a multiple alignment program. In some embodiments, the multiple alignment program is MAFFT. In some embodiments, the sequence alignment program is a whole genome alignment program. In some embodiments, the whole genome alignment is performed using BLASTN. In some embodiments, BLASTN is utilized without any changes to the default parameters.

To express the enzymes of the present invention using recombinant technology, a polynucleotide encoding the enzymes is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

The polynucleotide may further comprise ribosome binding sites to differentially control the expression level of the genes. Thus, for example for rbcL, the ribosome binding site rbs-C may be used, for prkA the ribosome binding site rbs-E may be used and for CA the ribosome binding site rbs-C may be used.

Thus, the present invention contemplates isolated polynucleotides encoding the enzymes of the present invention.

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exon sequences required to encode the polypeptide of the present invention, as well as some intronic sequences interposing there between. The intronic sequences can be of any source, including of other genes, and typically will include conserved splicing signal sequences. Such intronic sequences may further include cis acting expression regulatory elements.

Nucleic acid sequences encoding the enzymes of some embodiments of the invention may be optimized for expression for a particular microorganism. Examples of such sequence modifications include, but are not limited to, an altered G/C content to more closely approach that typically found in the microorganism species of interest, and the removal of codons atypically found in the microorganism species commonly referred to as codon optimization.

The phrase "codon optimization" refers to the selection of appropriate DNA nucleotides for use within a structural gene or fragment thereof that approaches codon usage within the microorganism of interest. Therefore, an optimized gene or nucleic acid sequence refers to a gene in which the nucleotide sequence of a native or naturally occurring gene has been modified in order to utilize statistically-preferred or statistically-favored codons within the microorganism. The nucleotide sequence typically is examined at the DNA level and the coding region optimized for expression in the microorganism species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed genes, followed by a calculation of the average squared deviation. The formula used is: 1 SDCU=n=1 N [(Xn−Yn)/Yn]2/N, where Xn refers to the frequency of usage of codon n in highly expressed genes, where Yn to the frequency of usage of codon n in the gene of interest and N refers to the total number of codons in the gene of interest.

One method of optimizing the nucleic acid sequence in accordance with the preferred codon usage for a particular cell type is based on the direct use, without performing any extra statistical calculations, of codon optimization tables such as those provided on-line at the Codon Usage Database through the NIAS (National Institute of Agrobiological Sciences) DNA bank in Japan (www(dot)kazusa(dot)or(dot)jp/codon/). The Codon Usage Database contains codon usage tables for a number of different species, with each codon usage table having been statistically determined based on the data present in Genbank.

By using the above tables to determine the most preferred or most favored codons for each amino acid in a particular species (for example, E. Coli), a naturally-occurring nucleotide sequence encoding a protein of interest can be codon optimized for that particular species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively affect mRNA stability or expression.

The naturally-occurring encoding nucleotide sequence may already, in advance of any modification, contain a number of codons that correspond to a statistically-favored codon in a particular species. Therefore, codon optimization of the native nucleotide sequence may comprise determining which codons, within the native nucleotide sequence, are not statistically-favored with regards to a particular plant, and modifying these codons in accordance with a codon usage table of the particular species to produce a codon optimized derivative. A modified nucleotide sequence may be fully or partially optimized for microorganism codon usage provided that the protein encoded by the modified nucleotide sequence is produced at a level higher than the protein encoded by the corresponding naturally occurring or native gene. Construction of synthetic genes by altering the codon usage is described in for example PCT Patent Application No. 93/07278.

As mentioned hereinabove, polynucleotide sequences of the present invention are inserted into expression vectors (i.e., a nucleic acid construct) to enable expression of the recombinant polypeptide. The expression vector of the present invention includes additional sequences which render this vector suitable for replication and integration in pro-karyotes, eukaryotes, or preferably both (e.g., shuttle vectors). Typical cloning vectors contain transcription and translation initiation sequences (e.g., promoters, enhances) and transcription and translation terminators (e.g., polyade-nylation signals).

Various methods can be used to introduce the expression vector of the present invention into the host cell system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Bio-techniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Exemplary bacterial based expression systems are dis-closed in Baneyx et al., Current Opinion in Biotechnology, 1999; 10, 411-421 and Macrides et al, Microbiol Rev 1996, 60: 512-538, incorporated herein by reference.

Contemplated promoters for expression in bacteria include the 1-arabinose inducible araBAD promoter (PBAD), the lac promoter, the 1-rhamnose inducible rhaP BAD promoter, the T7 RNA polymerase promoter, the trc and tac promoter, the lambda phage promoter pL, and the anhydrotetracycline-inducible tetA promoter/operator.

Approaches for controlling the abundance of the above mentioned proteins include altering the promoter [K. Ham-mer, I. Mijakovic, P. R. Jensen, Synthetic promoter librar-ies—tuning of gene expression, Trends in Biotechnology 24, 53-55 (2006)] or the ribosome binding site (RBS) [H. M. Salis, E. A. Mirsky, C. A. Voigt, Automated design of synthetic ribosome binding sites to control protein expres-sion, Nat Biotechnol 27, 946-950 (2009); H. H. Wang et al., Programming cells by multiplex genome engineering and accelerated evolution, Nature 460, 894-898 (2009)] sequences, modulating the stability of transcripts and vary-ing the degradation rate of the mature protein.

The bacteria may be transformed stably or transiently with the nucleic acid constructs of the present invention. In stable transformation, the nucleic acid molecule of the present invention is integrated into the bacteria genome and as such it represents a stable and inherited trait. In transient transformation, the nucleic acid molecule is expressed by the cell transformed but it is not integrated into the genome and as such it represents a transient trait.

Knock-in methods for expressing a gene in a bacteria are also contemplated.

According to one embodiment, the recombinant bacteria requires a pentose or hexose sugar to generate biomass. Exemplary pentose or hexose sugars include for example glycerol or xylose.

According to another embodiment, the recombinant is an autotrophic bacteria.

As used herein, the term "autotrophic bacteria" refers to a bacteria that is capable of producing all its biomass carbon from $CO_2$.

In order to minimize utilization of an organic carbon source, down-regulation of the amount or activity of phos-phofructokinase (pfk).

Preferably down-regulation of both pfkA and pfkB (EC 2.7.1.105) is effected. In one embodiment, the genes pfkA and pfkB are knocked-out.

Glucose 6-phosphate-1-dehydrogenase (zwf) may be knocked out to prevent utilization of the oxidative P path-way.

According to a particular embodiment, the bacteria are engineered to comprise knock-outs of pfkA, pfkB and zwf.

Additional genes whose amount or activity may be down-regulated include pgi, prs aroH and eno. In one embodiment, the pgi, prs and/or aroH is knocked-out.

According to a specific embodiment, the bacteria com-prise at least one mutation in prs. Preferably, the mutation brings about a down-regulation of the amount and/or activity of the gene.

According to a specific embodiment, the bacteria com-prise at least one mutation in aroH or eno. Preferably, the mutation brings about a down-regulation of the amount and/or activity of the gene. In one embodiment, the aroH is knocked-out.

According to a specific embodiment, the bacteria com-prise at least one mutation in at least one of genes selected from the group consisting of RNA polymerase, beta subunit (rpoB), mal regulon transcriptional activator (malI) and poly(A) polymerase (pcnB). Preferably, the mutation brings about a down-regulation of the amount and/or activity of the gene. In one embodiment, the malT or pcnB is knocked-out.

According to a specific embodiment, the bacteria com-prise at least one mutation in each of the genes RNA polymerase, beta subunit (rpoB), mal regulon transcriptional activator (malI), poly(A) polymerase (pcnB) and pgi. Pref-erably, the mutation brings about a down-regulation of the amount and/or activity of the gene.

Additional mutations which can be effected in the bacteria of this aspect of the present invention are listed in Tables 4-9. Preferably, the mutation brings about a down-regulation of the amount and/or activity of the gene (e.g. by at least 10%, 20%, 30%, 40%, 50%, 60%, 70%, 80%, 90% or more).

In one embodiment, the bacteria has mutations or knock-outs in each of the genes listed in Table 4.

In one embodiment, the bacteria has mutations or knock-outs in each of the genes listed in Table 5.

In one embodiment, the bacteria has mutations or knock-outs in each of the genes listed in Table 6.

In one embodiment, the bacteria has mutations or knock-outs in each of the genes listed in Table 7.

In one embodiment, the bacteria has mutations or knock-outs in each of the genes listed in Table 8.

In one embodiment, the bacteria has mutations or knock-outs in each of the genes listed in Table 9.

Down-regulation of the amount (i.e. expression) or activ-ity of genes in the microorganism may be effected using any method known in the art.

Methods of deleting or downregulating genes from the chromosome of bacteria are known to those of skill in the art and include homologous recombination, knock out tech-niques, RNAi etc.

For bacteria, methods such as P1 transduction from already existing knockout strains (KEIO collection) or via lambda-phage assisted recombination (Pkd46 system) may be used to knock-out specific genes.

In one embodiment, the gene knockout is carried out using iterative rounds of P1 transductions. Exemplary methods of doing this are described in WO2015/177800, the contents of which are incorporated herein by reference.

Other methods which include down-regulating genes in bacteria using CRISPR arrays are also contemplated. These methods are described for example in WO 2012164565, the contents of which is incorporated herein by reference.

The present inventors have found that in order to generate bacteria that rely solely on carbon dioxide to supply the building blocks for biomass, it is preferable to initially culture the bacteria in a culture which comprises a hexose or pentose sugar (e.g. xylose). The gas atmosphere may be manipulated such that the carbon dioxide is provided at saturating levels (e.g. at a minimum of 2%). In one embodiment, the media is flushed with a gas mixture containing elevated concentrations of $CO_2$ (2% <$[CO_2]$<20%) throughout the cultivation.

Thus, according to another aspect of the present invention there is provided a method of generating an autotrophic bacteria comprising:

(a) obtaining a bacteria which expresses a recombinant formate dehydrogenase (FDH), phosphoribulokinase (prk) and Ribulose-Bisphosphate Carboxylase/oxygenase (RuBisCo), the bacteria being modified to down-regulate the amount or activity of zwf, pfkA and pfkB;

(b) culturing the bacteria in a medium comprising a pentose or hexose sugar; and subsequently (c) reducing the amount of the pentose or hexose sugar in the medium and increasing the amount of formate in the medium.

Preferably, the bacteria are grown (i.e. cultured) for at least one day, at least two days, at least three days, at least one week, at least one month, at least three months following genetic modification in order for the generation of new strains which are further adapted for autotrophic growth.

The amount of hexose or pentose sugar may be gradually reduced such that eventually, the bacteria relies solely on the carbon dioxide to supply the building blocks for biomass production, as further explained herein below.

Typically, the medium also comprises an electron acceptor such as nitrate, sulfate or oxygen at low levels (1-5%). The medium may also comprise appropriate salts, minerals, metals and other nutrients, such as vitamins. Bacteria of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

According to one embodiment, the bacteria are cultured on a solid surface—e.g. agarose plates.

The bacteria may be immobilized on to a solid surface—e.g. filters and the like.

According to another embodiment, the bacteria are cultured in a bioreactor—e.g. a chemostat to which fresh medium is continuously added, while culture liquid is continuously removed to keep the culture volume constant. Initially, the chemostat may comprise a pentose or hexose sugar which can be gradually replaced by formate such that after an amount of time, the bacteria is cultured solely in formate and the pentose or hexose sugar is completely absent (or only residual amounts remain). By harnessing the natural selection of the *E. Coli* to optimize and balance pathway activity towards establishing autotrophic growth, as described herein, the present inventors have generated populations of *E. Coli* with additional mutations. Thus, the present inventors propose deleting (or down-regulating) any one of the genes or intergenic sequences summarized in Tables 4-9 as well as those described herein above in order to generate additional bacteria of this aspect of the present invention.

Typically a source of energy and reducing power is also required for the sustenance of the bacteria.

Two exemplary candidates for providing bacteria with reducing power (and energy) are formate and phosphite.

According to a particular embodiment, formate is used as the source of energy/reducing power as further described in U.S. Application No. 61/913,940, the contents of which are incorporated herein by reference.

The formate which is used may come from any source—e.g., sodium formate, potassium formate, formic acid or formic acid anhydride etc.

Alternatively, and/or additionally, the formate may be generated using electricity. $CO_2$ can be directly reduced at the cathode (the electrons are derived from water splitting at the anode, for example) to generate formate at relatively high efficiency.

In order to generate the formate for use by the bacteria, the bacteria is placed in a bioreactor in a fluid (e.g., water). The cathode may optionally be placed inside the bioreactor in contact with the bacteria. Alternatively, the cathode may be placed in a separate container to the bioreactor and the formate may be channeled to the chamber comprising the bacteria. The fluid may contain other elements required by the bacteria for growth including for example salts, minerals, metals and other nutrients, such as vitamins.

Examples of such bioreactors and further methods are provided in Li et al. Science, 2012, Vol 335, page 1596, Rabaey et al, Current Opinion in Biotechnology, 2011, 22: 371-377; Lovley et al., Current Opinion in Biotechnology, 2011, 22: 441-448; Lovley D. R., Environmental microbiology reports, 2011, 3(1), 27-35; Nevin et al., Microbiology, May/June 2010 Volume 1 Issue 2; Rabaey et al., Applied and Industrial Microbiology, Nature Reviews, October 2010, Volume 8, page 706-716; each of which are incorporated herein by reference.

The electrodes may be fabricated from such conductive polymers and metallic materials including indium tin oxide (ITO), graphite, platinum and silver.

According to one embodiment, the bacteria is one that produces an industrially important product—e.g., a biofuel or a chemical (e.g. astaxanthin). Alternatively, or additionally, the bacteria expresses enzymes such that it is capable of producing an industrially important product—e.g., a biofuel. Alternatively, or additionally, the bacteria expresses an industrially important product—e.g., a recombinant protein. Additional industrial important products include antibiotics or other pharmaceutical, solvents, pigments, food additives, monomers for the plastic industry and industrially valuable polymers.

Biofuels include for example, an alcohol (e.g., methanol, ethanol, propanol, isobutanol, and n-butanol etc.), a hydrocarbon (e.g., an alkane such as methane, ethane, propane, butane, an alkene such as ethylene, propylene, isoprenes, an alkyne such as acetylene etc.) hydrogen, a biodiesel (long-chain alkyl (methyl, propyl or ethyl) esters), an aldehyde or ketones (e.g. acetone, formaldehyde, 1-propanal, etc.). The biofuel can be a solid, a liquid or a gas.

The recombinant protein may be any protein—e.g., a human protein used for medicinal purposes. Examples of such proteins include an antibody, insulin, interferon, growth hormone, erythropoietin, growth hormone, follicle stimulating hormone, factor VIII, low density lipoprotein receptor (LDLR) alpha galactosidase A and glucocerebrosidase.

As mentioned, in order to express recombinant proteins in the bacteria, polynucleotide sequences encoding same are inserted into expression vectors as described herein above.

It will be appreciated that other than containing the necessary elements for the transcription and translation of the inserted coding sequence (encoding the industrially useful polypeptide), the expression construct for expression of the industrially useful polypeptide can also include sequences engineered to optimize stability, production, purification, yield or activity of the expressed polypeptide.

Depending on the vector and host system used for production, resultant polypeptides of the present invention may either remain within the recombinant cell, secreted into the fermentation medium, secreted into a space between two cellular membranes, such as the periplasmic space in *E. Coli*; or retained on the outer surface of a cell or viral membrane.

Following a predetermined time in culture, recovery of the recombinant polypeptide is effected.

The phrase "recovering the recombinant polypeptide" used herein refers to collecting the whole fermentation medium containing the polypeptide and need not imply additional steps of separation or purification.

Thus, polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the polypeptide of the present invention and fused cleavable moiety. Such a fusion protein can be designed so that the polypeptide can be readily isolated by affinity chromatography; e.g., by immobilization on a column specific for the cleavable moiety. Where a cleavage site is engineered between the polypeptide and the cleavable moiety, the polypeptide can be released from the chromatographic column by treatment with an appropriate enzyme or agent that specifically cleaves the fusion protein at this site.

Recovery of biofuels may be recovered according to methods known in the art. Alcohols such as ethanol, methanol, and/or butanol may be recovered from liquid material by molecular sieves, distillation, and/or other separation techniques. For example, ethanol can be concentrated by fractional distillation to about 90% or about 95% by weight. There are several methods available to further purify ethanol beyond the limits of distillation, and these include drying (e.g., with calcium oxide or rocksalt), the addition of small quantities of benzene or cyclohexane, molecular sieve, membrane, or by pressure reduction.

Product gas, for example, as produced by anaerobic metabolism or photosynthesis, may be processed to separate the methane and/or hydrogen components. Methane, hydrogen, or biogas may be drawn off from the system as pipeline gas.

In accordance with the invention, methane and/or hydrogen may be recovered as a biofuel product. Methane may be recovered and/or purified from biogas by known methods and systems which are commercially available, including membrane systems known for separating gases on the basis of different permeabilities. See, for example, U.S. Pat. No. 6,601,543, which is hereby incorporated by reference. Alternatively, various methods of adsorption may be used for separating methane and hydrogen.

Other ways of collecting biofuel products including centrifugation, temperature fractionalization, chromatographic methods and electrophoretic methods.

In certain embodiments, the biofuel recovery/purification components may be integrated into the bacteria culturing system (e.g. bioreactor), for example, by connecting the respective device or apparatus to the gas or liquid effluents from the bioreactors. The purified biofuels and bioenergy products may be stoked in a separate container(s).

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Strains: An engineered ancestor strain for chemostat evolution was generated based on the *Escherichia coli* BW25113 strain (Grenier et al., 2014). P1 transduction was used (Thomason, Costantino and Court, 2007) to transfer knockout alleles from the KEIO strain collection (Baba et al., 2006) to the engineered strain, and to knock out the genes phosphofructokinase (pfkA and pfkB) and 6-phosphate-1-dehydrogenase (zwf). Following the transduction of each knockout allele, the $Km^R$ selection marker was removed by using the FLP recombinase encoded by the pCP20 temperature-sensitive plasmid (Cherepanov and Wackernagel, 1995). Loss of the selection marker and the temperature-sensitive plasmid were validated by replica-plating the screened colonies and PCR analysis of the relevant loci. The engineered ΔpfkA ΔRAB Δzwf strain was then transformed with the pCBB plasmid (Antonovsky et al., 2016) (accession number KX077536) and with a pFDH plasmid (Addgene plasmid #131706) with a constitutive promoter controlling the expression of the fdh gene. Following whole-genome sequencing, it was noted that the ancestral strain possessed the following four mutations— fusA T1251, lrhA Δ9 bp (85-93/939), and integration of a mobile insertion sequence (IS) element into the promoter region of the xylE gene (−21, position 4,232,204). These mutations were acquired during early handling of the strain prior to chemostat inoculation.

Plasmids: To create the pFDH plasmid, an *E. coli* codon optimized DNA sequence based on the amino acid sequence of formate dehydrogenase from the methytholotrophic bacterium *Pseudomonas* sp. 101 (Popov and Lamzin, 1994) was synthesized and cloned with an N-terminal his-tag into a pZE21-MCS plasmid (Expressys, Germany). The $P_{LtetO-1}$ promoter was replaced with a constitutive one driving medium transcription levels (clone #10 from (Braatsch et al., 2008)) and a strong ribosome binding site (rbs B of (Zelcbuch et al., 2013)). The $Km^R$ selection marker on the plasmid was replaced with the aadA gene, which confers resistance to streptomycin. Details regarding the pCBB plasmid are reported in (Antonovsky et al., 2016).

Growth media: Plasmid cloning and genomic modifications were carried out on a Luria Bertani medium with the relevant antibiotics (kanamycin (50 μg/ml), chloramphenicol (30 μg/ml, dissolved directly in the autoclaved M9 media and then filtered through a 0.22 μm PVDF filter) and/or streptomycin (100 μg/ml)). Engineered and evolved strains were grown on M9 minimal media supplemented with trace elements and the relevant carbon source(s). In the $^{13}$C-labeling experiments and for accurate estimation of growth parameters of the evolved cells on formate as the only organic compound, HPLC-grade water (Sigma Aldrich) was used and EDTA was omitted from the trace elements.

The trace elements components and their concentrations in the M9 media are: 50 mg/L EDTA (omitted during $^{13}$C labeling experiments and growth measurements), 31 μM $FeCl_3$, 6.2 μM $ZnCl_2$, 0.7611M $CuCl_2.2H_2O$, 0.42 μM $CoCl_2$-$6H_2O$, 1.62 μM $H_3BO_3$, 81 nM $MnCl_2·4H_2O$.

Growth tests: The growth experiments were conducted in a DASBox mini fermentation system (Eppendorf, Germany). The starting volume of each bioreactor was 150 ml M9 media supplemented with 30 mM or 35 mM sodium formate (Sigma Aldrich) as the carbon source, and trace elements (without the addition of EDTA and vitamin B1). Bacterial cells were seeded from a 15 ml starter at an $OD_{600}$ of 0.12-0.14 (resulting in a 1:10 dilution by volume). Growth temperature was set to 37° C., and the chemostat was aerated at a rate of 6 L/hr with 90% air supplemented with 10% $CO_2$. Values from the various probes were logged at 5 min intervals and used for analysis as described below. Once a day, 2 ml samples were removed from the bioreactor and used for media analysis (after filtration through a 0.22 micron PVDF Millex-GV syringe filter unit (Merck Millipore)) and for offline OD measurements (see below). Once the culture reached the stationary phase, ≈15 ml of the media were resuspended in fresh M9 media, as above, to a total of 150 ml, and the growth test was repeated.

Optical density measurements were performed online, using the integrated DASGIP® OD4 module and sensors. The values were converted into $OD_{600}$ by taking samples from the growth medium at various optical densities and measuring the $OD_{600}$ of each sample offline with a spectrophotometer (Ultrospec 10 Cell density meter, Amersham Biosciences) and a standard 10 mm polystyrene cuvette (Sarstedt, Germany).

A linear relation was fitted between the DASGIP® OD4 measurements and the $OD_{600}$ measurements. After diluting the cells, the DASGIP® OD4 module was calibrated to give a value of 0 at the beginning of the second growth test. In this case, a linear relation was fitted between $OD_{600}$ measurements of samples from the culture and the readings of the DASGIP® OD4 sensor, using the same slope as the one employed for the linear fit from the first growth test. Growth rates were determined by transforming $OD_{600}$ measurements into logarithmic scale with a base of 2 and then calculating the growth rate over a sliding window interval of 150 sample points, in each window fitting a linear relation between $\log_2(OD_{600})$ and time (in hours). The slope of each fit represents the estimated growth rate (in doublings per hour). Then, the average of the highest growth rate in the four experiments (two growth cycles for each of the two formate concentrations was calculated—30 mM and 35 mM) to give the best estimate of the maximal growth rate. The doubling time was calculated as the inverse of the growth rate, expressed in units of hours per doubling. To estimate the uncertainty of the calculated growth rates due to the calibration error, the inventors sub-sampled from the data to get 100 different linear relations (slopes and intercepts) between the DASGIP® OD4 measurements and the $OD_{600}$ measurements. For each sampled set of parameters, the growth rate was calculated based on the same procedure described above. The mean and standard deviation of these 100 growth rates were used as the best estimators of the growth rate and its standard deviation in each growth test. The calibration error in each experiment was propagated assuming the calibration error is correlated across experiments.

Yield calculation for autotrophic growth on formate: The yield was calculated based on the values of samples taken during the exponential phase of the growth according to the following equation:

$$Y = \frac{B(t) - B(t_0)}{S(t) - S(t_0)}, \qquad \text{(Equation 1)}$$

where B is the biomass weight in units of gram cell dry weight (gCDW) and S is the amount of formate in units of moles. The biomass weight was inferred from the measured optical densities of the samples at 600 nm ($OD_{600}$) via the conversion factor from $OD_{600}$ to gCDW, which ranges between 0.3 gCDW×$L^{-1}$ per $OD_{600}$ for *E. coli* cells (Glazyrina et al., 2010) to 0.5 gCDW×$L^{-1}$ per $OD_{600}$ (Folsom and Carlson, 2015). The mean value of 0.4±0.1 gCDW×$L^{-1}$ per $OD_{600}$ was used for the conversion.

Formate uptake rate calculation: Throughout each of the four growth experiments, the concentration of formate was measured in the growth medium at different time points by using both HPLC and an enzymatic assay (see Analysis of media composition section, herein below). The measured formate concentration was fitted over the course of each growth experiment with a four parameter logistic function of the form:

$$y(t) = \frac{a - d}{1 + \left(\frac{t}{c}\right)^b} + d, \qquad \text{(Equation 2)}$$

The derivative of the fitted logistic function was then calculated at each time point during the course of the growth to estimate the total formate consumption rate. The formate consumption rate was normalized to the amount of cellular biomass by using the $OD_{600}$ of the culture at the same time point, and converting it to dry cellular mass assuming a factor of 0.4 gCDW×$L^{-1}$ per $OD_{600}$. The mean uptake rate and its standard error across the four different growth tests (two growth cycles for each of the two formate concentrations—30 mM and 35 mM) is reported.

Chemostat evolution experiment: The evolution experiment was conducted in a Bioflo 110 chemostat (New Brunswick Scientific, USA) at a working volume of 0.7 L and a dilution rate of 0.02 $h^{-1}$ (equivalent to a doubling time of ≈33 hours) at 37° C. The chemostat was fed media containing 4 g/L sodium formate and 0.5 g/L D-xylose as sole carbon sources. This amount of xylose in the feed makes xylose the limiting nutrient for cell growth in the chemostat. On days 47, 166, 214, and 343 of the evolution experiment, the level of D-xylose in the feed media was reduced to 0.28, 0.13, 0.05, and 0 g/L, respectively. The concentration of formate was increased to 6 g/L on day 357, after the autotrophic growth phenotype was observed, and chloramphenicol (30 mg/L) and streptomycin (100 mg/L) were added to the feed media. Aeration of the chemostat was done through a DASGIP MX4/4 stand-alone gas-mixing module (Eppendorf, Germany) with a composition of 10% $CO_2$ and 90% air at a flow rate of 40 sL/hr. To monitor the chemostat, a weekly sampling protocol was performed. Samples were taken for media analysis and phenotyping (inoculation of the bacteria on minimal media containing formate and lacking D-xylose). The biomass dependency metric of each sample was calculated as the ratio between the xylose carbon concentration (g carbon/L) in the feed and the carbon concentration in the culture biomass. The biomass carbon concentration was calculated with a conversion factor of 0.2 g carbon per 1 $OD_{600}$ (Glazyrina et al., 2010; Folsom and Carlson, 2015). The optical density of each extracted sample was measured using a spectrophotometer (Ultrospec 10 Cell density meter, Amersham Biosciences) and a standard 10 mm polystyrene cuvette (Sarstedt, Germany).

$^{13}$C Isotopic labeling experiment: A culture of evolved cells grown on naturally labeled sodium formate in an elevated $CO_2$ (10%, naturally labeled) incubator (New Brunswick S41i $CO_2$ incubator shaker, Eppendorf, Germany) were diluted 8-fold into fresh M9 media with either 30 mM $^{12}$C or $^{13}$C-formate sodium salt (Sigma Aldrich) to a total volume of 10 ml of culture. In the "open" labeling setup, growth was carried out in 125 ml glass shake flasks with breathable sealing sticker-films (AeraSeal, Excel Scientific, USA), which allow free exchange of gases between the headspace of the growth vessel and the gas mixture of the incubator. The flasks were placed inside an elevated $CO_2$ (10%) shaker-incubator (New Brunswick) with 37° C. After ≈3 doublings, the cells were again diluted 8-fold into fresh media of the same type. This procedure was repeated several times for at least 10 doublings within each of the conditions.

Then, the cells were harvested for subsequent analysis of protein-bound amino acids and intracellular metabolites. In the "closed" labeling setup, growth was carried out in 250 ml glass shake flasks with a transparent extension, which allows the measurement of the optical density of the culture without opening it. After ≈3 doublings, the cells were diluted 8-fold into flasks covered with an air-tight rubber septa (SubaSeal, Sigma Aldrich). Then, the headspace of the flask was flushed with a gas mixture containing 10% $^{13}CO_2$ (Cambridge Isotope Laboratories, USA)+90% air or 10% $^{12}CO_2$+90% air generated by a DASGIP MX4/4 stand-alone gas-mixing module (Eppendorf, Germany). The flasks were then placed in a 37° C. shaker incubator. This procedure was repeated several times for at least 10 doublings for each of the conditions. Then, the cells were harvested for subsequent analysis of protein-bound amino acids and intracellular metabolites. The glass flasks used in the labeling experiments were pretreated by heating in a 460° C. furnace for 5 hours to evaporate any excess carbon sources that could remain in the vessels from previous utilizations. Number of replicates (growth flasks) in each condition with the evolved isolated clone: (a) $^{13}CO_2+^{13}C$-formate (n=3). (b) $^{13}CO_2+$ $^{12}C$-formate (n=5). (c) $^{12}CO_2+^{13}C$-formate (n=3). (d) $^{12}CO_2+^{12}C$-formate (n=1 for this trivial control). Number of replicates (growth flasks) in each condition with a sample taken from the chemostat after day 350: (a) $^{13}CO_2+^{13}C$-formate (n=3). (b) $^{13}CO_2+^{12}C$-formate (n=2). (c) $^{12}CO_2+$ $^{13}C$-formate (n=3). The labeling of WT *E. coli* cells using $U^{13}C_6$-glucose was performed with n=1 of this well established control.

Sample preparation for liquid chromatography coupled to mass spectrometry and mass analysis of biomass components: After harvesting the biomass, culture samples were prepared and analyzed as described in (Antonovsky et al., 2016). Briefly, for protein-bound amino acids, ≈3 ml of culture at $OD_{600}$ turbidity of ≈0.1-0.15 were pelleted by centrifugation for 5 minutes at 8,000 g. The pellet was suspended in 1 ml of 6N HCl and incubated for 24 hours at 110° C. The acid was subsequently evaporated with a nitrogen stream, resulting in a dry hydrolysate. Dry hydrolysates were resuspended in 0.6 ml of MilliQ water, centrifuged for 5 minutes at 14,000 g. The supernatant was then injected into the LCMS. Hydrolyzed amino acids were separated using ultra performance liquid chromatography (UPLC, Acquity—Waters, USA) on a C-8 column (Zorbax Eclipse XBD—Agilent, USA) at a flow rate of 0.6 mL/min and eluted off the column using a hydrophobicity gradient. Buffers used: A) $H_2O+0.1\%$ formic acid and B) acetonitrile+ 0.1% formic acid with the following gradient: 100% of A (0-3 min), 100% A to 100% B (3-9 min), 100% B (9-13 min), 100% B to 100% A (13-14 min), 100% A (14-20 min). The UPLC was coupled online to a triple quadrupole mass spectrometer (TQS—Waters, USA). Data was acquired using MassLynx v4.1 (Waters, USA). Amino acids and metabolites used for analysis were selected according to the following criteria: Amino acids were chosen that have peaks at a distinct retention time and m/z values for all isotopologues and also showed correct $^{13}C$ labeling fractions in control samples that contained protein hydrolyzates of WT cells grown with known ratios of $^{13}C_6$-glucose to $^{12}C$-glucose.

For intracellular metabolites, ≈8 ml of culture at $OD_{600}$ turbidity of ≈0.1-0.15 were pelleted by centrifugation for 5 minutes at 5,000 g. The pellet was suspended in 4 mL of a cold (−20° C.) acetonitrile:methanol:water (40:40:20) extraction solution and incubated overnight at this temperature. The next day, the extracts were centrifuged (5 minutes at 16,000 g), and the supernatant was transferred into fresh tubes. Organic solvents were subsequently evaporated using a speedvac vacuum concentrator. The aqueous phase was evaporated by freeze drying. Dry extracts were stored at −80° C. until the mass spectrometry analysis. Prior to injection into the mass spectrometer, the dry extracts were suspended in 200 pt of a 1:1 methanol:water solution, centrifuged (5 minutes at 16,000 g) and then the supernatant was transferred to a vial for injection. Metabolites were separated using liquid chromatography. A ZIC-pHILIC column (4.6 mm×150 mm, guard column 4.6 mm×10 mm; Merck) was used for liquid chromatography separation via a gradient elution with a solution of 20 mM ammonium carbonate, with 0.1% ammonium hydroxide, and acetonitrile at 0.1 mL/min. Detection of metabolites was performed using a Thermo Scientific Exactive high-resolution mass spectrometer with electrospray ionization, examining metabolites in a polarity switching mode over the mass range of 75-1,000 m/z. The identities of the compounds were verified by matching masses and retention times to a library of authenticated standards. Data analysis was performed using the Maven software suite (Clasquin, Melamud and Rabinowitz, 2012).

The $^{13}C$ fraction of each metabolite was determined as the weighted average of the fractions of all the isotopologues of the metabolite, as depicted in the equation below:

$$\% \ ^{13}C = \frac{\sum_{i=0}^{n} f_i * i}{n}, \quad \text{(Equation 3)}$$

where n is the number of carbons in the compound (e.g., for the amino acid serine, n=3) and $f_i$ is the relative fraction of the i-th isotopologue.

Calculation of the effective $^{13}C$ fraction of inorganic carbon in $^{13}C$ isotopic labeling experiments: The carbamoyl-phosphate moiety was used as a marker for the isotopic distribution of the intracellular inorganic carbon pool. Carbamoyl-phosphate is generated by carbamoyl phosphate synthetase from bicarbonate as the carbon substrate. Carbamoyl-phosphate is then condensed with ornithine in the L-arginine biosynthesis pathway. Mass isotopologue distribution of L-arginine, which contains an extra carbon from carbamoyl-phosphate (the guanidinium group carbon), versus the mass isotopologue distribution of either L-proline or L-glutamate, which are similar to that of ornithine. The effective $^{13}C$ labeling of intracellular inorganic carbon was calculated by using the following equation (written for glutamate but can be equivalently used with proline instead):

$$\text{effective } \% \ ^{13}CO_2 = \sum_{i=0}^{6} f_{arg_i} * i - \sum_{i=0}^{5} f_{glu_i} * i, \quad \text{(Equation 4)}$$

where $f_i$ is the relative fraction of the isotopologue (the subscripts arg and glu denote arginine and glutamate, respectively) and we sum over all isotopologues (equal to the number of carbon atoms in the compound, 6 for arginine and 5 for proline or glutamate). The calculation was repeated using the measured isotopologue fractions of proline instead of those of glutamate. The average of those two calculations was used as a more robust estimator of the level of $^{13}CO_2$ and the associated uncertainty. The computed labeled fraction was then used to normalize the $^{13}C$-labeled fractions of all the measured metabolites using the following equation:

$$\text{corrected } \% \ ^{13}C-met_i = \frac{\text{measured } ^{13}C-met_i}{\text{effective } \% \ ^{13}CO_2}, \quad \text{(Equation 5)}$$

where $met_i$ stands for each of the measured metabolites and protein-bound amino acids. An analogous correction procedure using the labeled fractions aspartate and carbamoyl-aspartate was performed in a recent study (Bennett et al., 2008) to account for incomplete labeling owing to incorporation of non-labeled inorganic carbon in the media.

Whole-genome sequencing: DNA extraction (DNeasy blood & tissue kit, Qiagen) and library preparation procedures were carried as previously described in (Herz et al., 2017). Tagging and fragmenting ('tagmentation') using the Nextera kit (Illumina kits FC-121-1031) was performed by mixing 1 μl containing 1.5 ng of genomic DNA, 1.25 μl of TD buffer, and 0.25 μl of TDE1. The mixture was mixed gently by pipetting and placed for incubation in a thermo-cycler for 8 min at 55° C. Next, "tagmented" gDNA underwent PCR-mediated adapter addition and library amplification by mixing 11 μl of PCR master mix (KAPA KK2611/KK2612), 4.5 μl of 5 μM index1 (Nextera index kit FC-121-1011), 4.5 μl of 5 μM index2, and 2.5 μl of tag-mented DNA in each well. The final total volume per well was 22.5 μl. The thermocycler was run with the following program: 1) 72° C. for 3 min, 2) 98° C. for 5 min, 3) 98° C. for 10 s, 4) 63° C. for 30 s, and 5) 72° C. for 30 s. 6) Repeat steps (3)—(5) 13 times for a total of 13 cycles. 7) 72° C. for 5 min. 8) Hold at 4° C. PCR cleanup and size selection were done in several steps: mixing 12 μl of magnetic beads spriSelect reagent (Beckman Coulter B23317) with 15 μl of each PCR reaction. Incubation at room temperature for 5 min followed by 1 min on a magnetic stand. The clear solution was discarded, and the beads were mixed with 200 μl of freshly made 80% ethanol. An ethanol wash was performed twice, and the plate was then incubated at room temperature for 5 min to allow for the evaporation of residual ethanol. The sample was eluted with 30 μl of ultrapure water for 5 min at room temperature, and the beads were removed using the magnetic stand. The prepared libraries were sequenced by a Miseq machine (Illumina). Analysis of the sequencing data was performed as previously described in (Antonovsky et al., 2016; Herz et al., 2017) using the breseq software (Barrick et al., 2014) with genomic and plasmid DNA sequences as references for alignments of sequencing reads.

To exclude the possibility of contamination in the different experiments, the DNA was extracted from bacterial pellets taken at the end of the experiments, sequenced as described and validated that following alignment of the sequencing reads to the reference genome and plasmid sequences; at least 95% of the reads were aligned.

Analysis of media composition: Media samples collected during the evolution experiment and batch-growth experiments were first filtered through a 0.22 micron PVDF Millex-GV syringe filter unit (Merck Millipore), and stored at −80° C. After thawing, the media samples they were analyzed with an Agilent 1200 high-performance liquid chromatography system (Agilent technologies, USA) equipped with a refractive index detector and an anion exchange Bio-Rad HPX-87H column (Bio-Rad, USA). The column was eluted with 5 mM sulfuric acid at a flow rate of 0.6 mL/min at 45° C. Samples with a formate concentration below the detection limit of the HPLC were analyzed by an enzymatic assay kit (Megazyme, Ireland). Media samples from the evolution experiments were each measured once. Media samples from the batch growth experiments were measured 3 times, with the mean±S.D. is shown in FIG. 2C. The samples analyzed with the enzymatic kit were measured twice; the mean±S.D. is reported.

In silico analysis of autotrophic E. coli growth: For the flux balance analysis of the E. coli strains, the Core Escherichia coli Metabolic Model (Orth et al., 2010), and added the rubisco, prk, and fdh reactions. Then, the following changes were made to the model:

PFK, ZWF (G6PDH2r in the code model), and PFL were knocked out

The rate bounds for RBC, PRK, and FDH were set to the default values, i.e. to 0-1000 mmol/g/h All carbon-containing export/import reactions were removed, except for formate and $CO_2$ (which were left unbounded, i.e. −1000 to 1000 mmol/g/h)

We assumed that all formate uptake is done by diffusion, i.e. via the reaction FORt. Therefore, we set the bounds on FORt2 (formate proton symporter) to 0, and the bounds for FORt to 19±2 mmol/g/h (based on the measured total formate uptake rates).

Based on the measured values, the growth rate bounds were set to: 0.04±0.01 h$^{-1}$.

The resulting model was then used to generate a Phenotypic Phase Plane. Such plots depict the feasible space where flux solutions exist given the flux balance analysis constraints. In FIG. 5A, formate uptake rate is the controlled parameter (relaxing the constraint mentioned above), and the range of possible net $CO_2$ production rates is shown on the y-axis. The rate of FDH is completely determined by the formate uptake since it is the only reaction that can metabolise formate in the core model. The net $CO_2$ production rate can still vary slightly depending on the growth rate (which is a function of how much of the $CO_2$ is fixed by Rubisco).

Even when setting the formate uptake rate to the measured value (19±2 mmol/g/h), there is still some redundancy in the flux solution space (due to the uncertainty ranges and also the stoichiometry itself). Therefore, the objective of minimum sum of fluxes was used (also known as parsimonious flux balance analysis, or pFBA) to get a unique flux solution (Holzhütter, 2004). For the minimum sum of fluxes solution, the growth rate is at its upper limit (0.05 l/h) and the formate uptake rate is at its lower limit (17 mmol/gCDW/h). The net production is calculated by the difference between all decarboxylating reactions and all carboxylating ones. This calculation may be visualized by a stacked bar plot in FIG. 5B. Since all energy and reducing potential comes from formate, it can be seen that FDH is responsible for almost all of the decarboxylations, and greatly surpasses the amount of carboxylations (mainly performed by rubisco) which sum up to 2.4 mmol/gCDW/h. Therefore, there is a positive net $CO_2$ production of about 15 mmol/gCDW/h.

Finally, the net rate of carbon fixation for the evolved strain was analyzed when the formate is produced electro-chemically from $CO_2$. In this case, all $CO_2$ produced by FDH cancels out, and the net $CO_2$ fixation rate is 2.1 mmol/gCDW/h, where only about 13% of the carbon fixed by RBC and PPC is released as $CO_2$ in PDH, ICD, and ME1 (FIG. 5C). All calculations were done using COBRApy (Ebrahim et al., 2013).

Results

Metabolic Rewiring and Lab Evolution for Conversion to Autotrophy

In order to convert E. coli to autotrophy in the laboratory, several candidate compounds (Claassens et al., 2018) were considered as electron donors for $CO_2$ fixation. Formate was chosen as the electron source as this one-carbon organic compound can serve as a source of reducing power (Berms-Rivera, Bennett and San, 2002) but does not naturally support the growth of E. coli and is not assimilated into biomass. Its reduction potential (E$^0$=−420 mV) is low enough to reduce NAD$^+$, the main electron carrier in the cell (E$^0$=−280 mV under physiological conditions in E. coli (Huang et al., 2012)). Another advantage is that it can be electrochemically produced from renewable sources (Yishai et al., 2016) and is seen as a promising path for carbon negative biomass formation. To harvest the electrons from formate and direct them into the main cellular reducing power reservoir NADH, an NAD⁺-coupled formate dehy-drogenase (FDH; EC 1.17.1.9) from the methylotrophic bacterium Pseudomonas sp. 101 (Egorov et al., 1980) was used. Stoichiometric analysis of the metabolic network in *E. coli* (Orth, Thiele and Palsson, 2010) suggests that the addition of FDH, Rubisco and phospho-ribulo-kinase (Prk) to the metabolic network of *E. coli* is sufficient for in-silico autotrophic growth (Volpers et al., 2016) in M9 minimal medium with formate and $CO_2$ as cosubstrates (FIG. 1). Yet, co-expression of the three recombinant enzymes in a naive BW25113 *E. coli* strain did not result in growth in auto-trophic conditions. The stoichiometric analysis does not take into account requirements such as tuning enzyme kinetics, expression level and regulation. Therefore, it was decided to use adaptive laboratory evolution as a metabolic optimiza-tion tool (Antonovsky et al., 2016) to achieve autotrophic growth.

The basic rationale behind the approach is as follows: Heterologous expression of non-native enzymatic machin-ery expands the space of possible metabolic reactions for the cell, enabling autotrophic growth. However, this does not guarantee that the needed flux will flow through the newly expanded set of reactions. In fact, as the central metabolism of *E. coli* is adapted to heterotrophic growth, it is likely that flux distribution that supports heterotrophic growth would continue to be utilized. To drive flux towards the desired metabolic pathway, adaptive laboratory evolution was employed. This approach combines rewiring central metabolism to establish a dependence on the Rubisco car-boxylation flux, tailoring the growth medium to inhibit flux through the native heterotrophic pathways, and providing a significant selective advantage to utilizing autotrophic path-ways. This should lead to the needed tuning of enzyme activity in a way that will divert flux to autotrophic path-ways. The way in which this approach was implemented is shown in FIG. 2A. First, three genes encoding two enzymes in central carbon metabolism: phosphofructokinase (Pfk) in glycolysis and glucose-6-phosphate-dehydrogenase (Zwf) were knocked out in the oxidative pentose-phosphate path-way. The former has two isoenzymes encoded by two genes (pfkA and pfkB). When growing cells on xylose, this rewir-ing ensures that cellular growth is dependent on carboxy-lation by Rubisco (Antonovsky et al., 2016) (FIGS. 6A-E). Second, Rubisco, Prk, carbonic anhydrase (CA, which inter-converts $CO_2$ and bicarbonate) and FDH were expressed in the cells. Third, the cells were grown in xylose-limited chemostats, which maintain cells in constant starvation for organic sugar carbon. This growth medium allows cells to proliferate, which is essential for evolution to take place, but inhibits the flux through heterotrophic catabolic pathways. The chemostat also contained an excess of formate and was constantly sparged with $CO_2$-enriched (10%) air. Thus, conditions were created in which cells that accumulate mutations leading to diversion of flux to the autotrophic pathway are selected. Such cells will reduce their depen-dence on the external organic sugar carbon input, and gain a large selective advantage compared to the non-mutated cells, which are limited by the supply of xylose. A dilution rate of 0.02 h⁻¹ was used.

Upon inoculation of the engineered strain into the xylose-limited chemostat with excess levels of formate, the residual levels of xylose dropped below the detection level, as expected under carbon-limited chemostat growth. Samples were extracted from the chemostat once a week and tested for growth in autotrophic conditions. Specifically, these are chemo-organo-autotrophic conditions for *E. coli*, which consist of minimal M9 media supplemented with 30 mM sodium formate in an elevated $CO_2$ (10%) atmosphere but without any other carbon source. Methylotrophs could potentially grow heterotrophically in such conditions, but the system was continuously monitored for the possibility of such contamination. After ≈200 days of chemostat propa-gation, equivalent to ≈150 chemostat generations, growth in media devoid of xylose was observed (autotrophic condi-tions). This phenotype persisted in all samples taken from that day on. Starting at day ≈350 of the chemostat adaptive laboratory evolution experiment, xylose was omitted from the feed media altogether as shown in FIG. 2B. The sus-tained growth and turbidity implied full takeover by xylose-independent cells in the chemostat. Growth of the extracted samples was validated by repeatedly re-diluting them into fresh xylose-free media. The samples required elevated $CO_2$ for growth, suggesting a carbon fixation growth mechanism. One of the isolated clones that showed more robust growth was chosen for in-depth characterization and exhibited a doubling time of 18±4 hours in autotrophic conditions, as shown in FIGS. 2C and 7. The cells had a formate-to-biomass conversion yield of 2.8±0.8 gCDW/mol formate, similar to microorganisms that naturally grow autotrophi-cally on formate (Pronk et al., 1991; Grunwald et al., 2015).

Labeling by ¹³C Demonstrates that all Biomass Carbon is Derived from $CO_2$

To test whether the evolved cells are indeed autotrophic and eliminate the possibility of unaccounted-for carbon sources or significant heterotrophic formate assimilation, comprehensive isotopic labeling experiments were con-ducted. First, one of the evolved clones was grown in an environment with ¹³C-labeled formate and ¹³CO₂ for ≈10 generations (until isotopic steady state) and the ¹³C labeling patterns of various metabolites was analyzed using LC/MS (Zamboni and Sauer, 2009). Biomass building blocks across central metabolism had ≈98% of their carbon atoms labeled (FIGS. 3B and 7, Table 1).

TABLE 1

¹³C-labeled fractions of protein-bound amino acids and sugar-phosphates following isotopic labeling experiment with ¹³CO₂ + ¹³C-formate

| Metabolite | Isolated Clone measured %¹³C | repeats | Mixed Population measured %¹³C | repeats |
|---|---|---|---|---|
| Ser | 99.3 ± 0.1% | n = 3 | 96.8 ± 1.4% | — |
| His | 98.9 ± 0.2% | n = 3 | 95.8 ± 1.6% | n = 3 |
| Val | 99.2 ± 0.03% | n = 3 | 97.5 ± 0.9% | n = 3 |
| Thr | 98.5 ± 0.7% | n = 3 | 93.6 ± 3.1% | n = 3 |
| Pro | 97.7 ± 0.3% | n = 3 | 92.4 ± 2.7% | n = 3 |
| Leu | 98.2 ± 0.3% | n = 3 | 93.2 ± 2.5% | n = 3 |
| Ile | 99.1 ± 0.03% | n = 3 | 97.5 ± 0.9% | n = 3 |
| Arg | 97.6 ± 0.3% | n = 3 | 92.3 ± 2.3% | n = 3 |
| Glu | 97.4 ± 0.4% | n = 3 | 91.0 ± 2.6% | n = 3 |
| S7P | 97.9 ± 1.1% | n = 3 | 98.4 ± 0.2% | n = 3 |
| P5P | 97.9 ± 0.5% | n = 3 | 97.3 ± 0.7% | n = 3 |
| H6P | 95.0 ± 2.1% | n = 3 | 96.0 ± 1.6% | n = 3 |
| AMP/ADP/ATP | 98.9 ± 0.3% | n = 3 | 99.1 ± 0.2% | n = 2 |
| UMP/UDP/UTP | 99.7 ± 0.3% | n = 3 | 99.2 ± 0.4% | n = 2 |

This is in line with the labeled formate and $CO_2$ com-prising ≈99% ¹³C and ≈1% unlabeled bicarbonate dissolved in the growth media. This provides definitive evidence that the cells' biomass carbon is derived solely from $CO_2$ and formate. To test whether formate is directly assimilated into biomass, the evolved cells were grown in minimal M9 media supplemented with ¹³C-labeled formate. The cultures were grown in a vessel with an air permeable cover inside a shaking incubator with elevated $CO_2$ (10%, naturally labeled). The ¹³C labeling pattern of biomass building blocks following growth in this environment showed 1-2% ¹³C labeling (FIGS. 3B and 8A-B, Table 2), which is the value expected based on the natural abundance of ¹³C plus minor amounts of labeled formate being oxidized to ¹³CO₂ and then fixed before equilibrating with the overall ¹²CO₂ pool.

TABLE 2

¹³C-labeled fractions of protein-bound amino
acids and sugar-phosphates following isotopic labeling experiment
with ¹²CO₂ + ¹³C-formate

| | Isolated Clone | | Mixed Population | |
|---|---|---|---|---|
| Metabolite | measured %¹³C | repeats | measured %¹³C | repeats |
| Ser | 1.0 ± 0.5% | n = 3 | n/a | — |
| His | 1.5 ± 0.1% | n = 3 | 1.3 ± 0.1% | n = 3 |
| Val | 1.5 ± 0.1% | n = 3 | 1.3 ± 0.1% | n = 3 |
| Thr | 1.4 ± 0.4% | n = 3 | 1.6 ± 0.1% | n = 3 |
| Pro | 1.7 ± 0.1% | n = 3 | 1.4 ± 0.03% | n = 3 |
| Leu | 1.4 ± 0.2% | n = 3 | 1.1 ± 0.03% | n = 3 |
| Ile | 1.3 ± 0.1% | n = 3 | 1.2 ± 0% | n = 3 |
| Arg | 1.8 ± 0.1% | n = 3 | 1.9 ± 0.03% | n = 3 |
| Glu | 2.0 ± 0.1% | n = 3 | 2.1 ± 0.1% | n = 3 |
| S7P | 1.2 ± 0.1% | n = 3 | 1.6 ± 0.1% | n = 3 |
| P5P | 1.2 ± 0.03% | n = 3 | 1.2 ± 0.2% | n = 3 |
| H6P | 1.3 ± 0.04% | n = 3 | 1.4 ± 0.1% | n = 3 |
| AMP/ADP/ATP | 11.2 ± 0.3% | n = 3 | n/a | |
| UMP/UDP/UTP | 0.4 ± 0.3% | n = 3 | n/a | |

These results demonstrate that the evolved cells practically do not assimilate formate. One very minor exception is the incorporation of carbon from formate into one of the carbons of the purine rings. However, this is not a necessity of the de novo purine biosynthetic pathway but rather a technical issue, as the formyl moiety can either originate from formate, if it is present in the media, or from 10-formyl-tetrahydrofolate, which originates from serine. The finding of negligible formate assimilation, together with the previous results indicating that there is no carbon source beyond CO₂ and formate entering the biomass, serves as strong evidence that the evolved *E. coli* cells are indeed autotrophic.

In another validation experiment, the cells were grown in vessels with labeled ¹³CO₂ and unlabeled formate. This experiment was performed in closed vessels, which leads to some accumulation of unlabeled CO₂ that is generated from oxidized formate, thus "polluting" the labeled ¹³CO₂ pool. This can be monitored and corrected for by analysis of the labeling of glutamate (or proline) versus arginine, as the latter is produced from the former by the addition of CO₂ (in the form of soluble bicarbonate; see FIGS. 9A-B and methods). Biomass building blocks across central metabolism had 85-90% of their carbon atoms labeled. As shown in FIGS. 3A and 3B, when correcting for the effective labeling of intracellular CO₂, the ¹³C-labeled fraction of the biomass building blocks is close to 100%, showing in an independent and detailed manner the autotrophic nature of the evolved *E. coli*. All the labeling experiments described above were repeated both for cells from an isolated clone and on a mixed population sample from the chemostat, yielding practically identical results, depicted in Table 3.

TABLE 3

¹³C-labeled fractions of protein-bound amino acids and sugar-phosphates
following isotopic labeling experiments with ¹³CO₂ + ¹²C-formate.

| | Isolated Clone | | | Mixed Population | | |
|---|---|---|---|---|---|---|
| Metabolite | measured | normalized | repeats | measured | normalized | repeats |
| Ser | 89.2 ± 2.6% | 99.9 ± 3.1% | n = 5 | 92.1 ± 2.7% | 100* ± 3.5% | n = 2 |
| His | 86.5 ± 1.3% | 97.0 ± 3.9% | n = 5 | 89.0 ± 3.3% | 98.0 ± 3.4% | n = 2 |
| Val | 89.6 ± 1.4% | 100* ± 3.8% | n = 5 | 92.4 ± 3.3% | 100* ± 3.5% | n = 2 |
| Thr | 88.5 ± 1.5% | 99.3 ± 4.2% | n = 5 | 90.2 ± 2.8% | 99.3 ± 3.5% | n = 2 |
| Pro | 85.9 ± 4.1% | 96.3 ± 6.6% | n = 5 | 87.2 ± 2.4% | 96.0 ± 3.3% | n = 2 |
| Leu | 86.0 ± 3.5% | 96.4 ± 5.9% | n = 5 | 87.5 ± 2.3% | 96.3 ± 3.4% | n = 2 |
| Ile | 87.9 ± 1.9% | 98.5 ± 4.0% | n = 5 | 89.8 ± 2.8% | 98.8 ± 3.4% | n = 2 |
| Arg | 86.0 ± 3.0% | 96.4 ± 5.4% | n = 5 | 87.1 ± 2.5% | 95.9 ± 3.3% | n = 2 |
| Glu | 84.7 ± 3.6% | 95.0 ± 6.4% | n = 5 | 86.0 ± 2.2% | 94.6 ± 3.3% | n = 2 |
| S7P | 84.8 ± 1.1% | 95.1 ± 4.3% | n = 5 | 82.7 ± 4.1% | 91.1 ± 3.1% | n = 2 |
| P5P | 83.9 ± 1.5% | 94.1 ± 4.7% | n = 5 | 80.7 ± 5.7% | 88.9 ± 3.1% | n = 2 |
| H6P | 83.5 ± 3.8% | 93.7 ± 6.1% | n = 5 | 81.8 ± 2.2% | 90.0 ± 3.1% | n = 2 |
| AMP/ADP/ATP | 77.2 ± 1.4% | 86.6 ± 4.3% | n = 5 | 74.0 ± 1.8% | 84.1 ± 3.2% | n = 2 |
| UMP/UDP/UTP | 87.1 ± 1.2% | 97.6 ± 4.5% | n = 5 | 84.2 ± 4.8% | 95.7 ± 6.1% | n = 2 |

The presented values are mean (±S.D.).
*Values that after normalization slightly exceeded 100% were written as 100%.

Laboratory Evolution Facilitated the Conversion to Autotrophy Via a Relatively Small Number of Mutations To better elucidate the genetic basis for the trophic-mode conversion to autotrophy, six clones capable of autotrophic growth on formate were isolated from the chemostat and their genome and plasmids were sequenced (List of mutations specified in Tables 4-9). Two of the clones were isolated while xylose was still present in the feed media (around day 250 of the evolutionary experiment, clones #1 & #2) and three after xylose was omitted from the chemostat feed media (around day 400 of the evolutionary experiment, clones #3, #4 & #5). A sixth clone was isolated after propagating one of the earlier isolated clones (clone #1) for several rounds of serial dilution (clone #6). Strikingly, as shown in FIG. 4, relatively few mutations fixed in the autotrophic clones (on top of the ancestral genetic background) were observed. The mutated genes can be divided into three broad categories.

TABLE 4

| | | | | | |
|---|---|---|---|---|---|
| | | | mutations identified in evolved clone #1 | | |
| chromosome | position | mutation | annotation | gene | description |
| *E. coli* genome | 155,132 | C→G | R161P(CGC→CCC) | pcnB | poly(A) polymerase |
| *E. coli* genome | 188,740 | C→G | I133M(ATC→ATG) | pyrH | uridylate kinase |
| *E. coli* genome | 407,471 | C→T | W156*(TGG→TAG) | araJ← | arabinose-inducible putative transporter, MFS family |
| *E. coli* genome | 567,750 | IS2(−) +5 bp | intergenic (+43/−70) | ybcM→/ →ylcH | DLP12 prophage; putative DNA-binding transcriptional regulator/uncharacterized protein, DLP12 prophage |
| *E. coli* genome | 1,783,016 | G→A | D109N(GAT→AAT) | aroH→ | 3-deoxy-D-arabino-heptulosonate-7-phosphate synthase, tryptophan repressible |
| *E. coli* genome | 3,208,093 | T→C | F563S(TTC→TCC) | rpoD→ | RNA polymerase, sigma 70 (sigma D) factor |
| *E. coli* genome | 3,547,518 | G→A | E359K(GAA→AAA) | malT→ | mal regulon transcriptional activator |
| *E. coli* genome | 3,729,347 | G→A | E337K(GAG→AAG) | xylR→ | xylose divergent operon transcriptional activator |
| *E. coli* genome | 4,173,770 | T→G | D866E(GAT→GAG) | rpoB→ | RNA polymerase, beta subunit |
| *E. coli* genome | 4,224,841 | C→T | H386Y(CAC→TAC) | pgi→ | glucosephosphate isomerase |
| pFDH plasmid | 918 | Δ8 bp | intergenic (−126/−86) | strepR←/ →pseudFDH | streptomycin resistance gene/formate dehydrogenase |

TABLE 5

| | | | | | |
|---|---|---|---|---|---|
| | | | mutations identified in evolved clone #2 | | |
| chromosome | position | mutation | annotation | gene | description |
| *E. coli* genome | 155,132 | C→G | R161P(CGC→CCC) | pcnB← | poly(A) polymerase |
| *E. coli* genome | 188,740 | C→G | I133M(ATC→ATG) | pyrH→ | uridylate kinase |
| *E. coli* genome | 407,471 | C→T | W156*(TGG→TAG) | araJ← | arabinose-inducible putative transporter, MFS family |
| *E. coli* genome | 1,782,894 | C→A | A68E(GCA→GAA) | aroH→ | 3-deoxy-D-arabino-heptulosonate-7-phosphate synthase, tryptophan repressible |
| *E. coli* genome | 3,208,093 | T→C | F563S(TTC→TCC) | rpoD→ | RNA polymerase, sigma 70 (sigma D) factor |
| *E. coli* genome | 3,547,518 | G→A | E359K(GAA→AAA) | malT→ | mal regulon transcriptional activator |
| *E. coli* genome | 3,729,347 | G→A | E337K(GAG→AAG) | xylR→ | xylose divergent operon transcriptional activator |
| *E. coli* genome | 3,933,885 | G→T | L30I(CTT→ATT) | hsrA← | putative multidrug or homocysteine efflux system |
| *E. coli* genome | 4,173,770 | T→G | D866E(GAT→GAG) | rpoB→ | RNA polymerase, beta subunit |
| *E. coli* genome | 4,224,841 | C→T | H386Y(CAC→TAC) | pgi→ | glucosephosphate isomerase |
| pFDH plasmid | 899 | IS1(−) +8 bp | intergenic (−107/−105) | strepR←/ →pseudFDH | streptomycin resistance gene/formate dehydrogenase |
| pFDH plasmid | 918 | Δ8 bp | intergenic (−126/−86) | strepR←/ →pseudFDH | streptomycin resistance gene/formate dehydrogenase |

TABLE 6

| | | | | | |
|---|---|---|---|---|---|
| | | | mutations identified in evolved clone #3 | | |
| chromosome | position | mutation | annotation | gene | description |
| *E. coli* genome | 103,910 | (CTTCCAGGAC - SEQ ID NO: 9)1→2 | coding (867/918 nt) | lpxC→ | UDP-3-O-acyl N-acetylglucosamine deacetylase |
| *E. coli* genome | 155,132 | C→G | R161P(CGC→CCC) | pcnB← | poly(A) polymerase |
| *E. coli* genome | 354,080 | Δ9 bp | coding (314-322/900 nt) | cynR← | transcriptional activator of cyn operon; autorepressor |
| *E. coli* genome | 407,471 | C→T | W156*(TGG→TAG) | araJ← | arabinose-inducible putative transporter, MFS family |
| *E. coli* genome | 829,599 | G→T | M358I(ATG→ATT) | dinG→ | ATP-dependent DNA helicase |
| *E. coli* genome | 1,104,830 | IS element integration | loss of function | opgG | osmoregulated periplasmic glucan (OPG) biosynthesis periplasmic protein |
| *E. coli* genome | 2,681,289 | C→A | D292Y(GAT→TAT) | glrR← | response regulator regulating glmY sRNA in two-component system with sensor protein GlrK |

TABLE 6-continued

| | | mutations identified in evolved clone #3 | | | |
|---|---|---|---|---|---|
| chromosome | position | mutation | annotation | gene | description |
| E. coli genome | 2,901,251 | C→A | G17V(GGT→GTT) | eno← | enolase |
| E. coli genome | 3,208,093 | T→C | F563S(TTC→TCC) | rpoD→ | RNA polymerase, sigma 70 (sigma D) factor |
| E. coli genome | 3,433,439 | C→A | R317L(CGC→CTC) | rpoA← | RNA polymerase, alpha subunit |
| E. coli genome | 3,547,518 | G→A | E359K(GAA→AAA) | malT→ | mal regulon transcriptional activator |
| E. coli genome | 3,729,347 | G→A | E337K(GAG→AAG) | xylR→ | xylose divergent operon transcriptional activator |
| E. coli genome | 4,173,770 | T→G | D866E(GAT→GAG) | rpoB→ | RNA polymerase, beta subunit |
| E. coli genome | 4,209,763-4,232,203 | large (22,441 bp) chromosomal deletion | | 17 genes: aceK, arpA, iclR, metH, yjbB, pepE, rluF, yjbD, lysC, pgi, yjbE, yjbF, yjbG, yjbH, yjbT, psiE, xylE | |
| E. coli genome | 4,275,144 | C→T | intergenic (−3/+197) | yjcH←/←acs | DUF485 family inner membrane protein/acetyl-CoA synthetase |
| E. coli genome | 4,276,215 | C→A | R362L(CGC→CTC) | acs← | acetyl-CoA synthetase |
| E. coli genome | 4,629,517 | C→T | V203M(GTG→ATG) | arcA← | response regulator in two-component regulatory system with ArcB or CpxA |
| pFDH plasmid | 901 | Δ5 bp | intergenic (−109/−106) | strepR←/→pseudFDH | streptomycin resistance gene/formate dehydrogenase |

TABLE 7

| | | mutations identified in evolved clone #4 | | | |
|---|---|---|---|---|---|
| chromosome | position | mutation | annotation | gene | description |
| E. coli genome | 103,910 | (CTTCCAGGAC - SEQ ID NO: 9)1→2 | coding (867/918 nt) | lpxC→ | UDP-3-O-acyl N-acetylglucosamine deacetylase |
| E. coli genome | 155,132 | C→G | R161P(CGC→CCC) | pcnB← | poly(A) polymerase |
| E. coli genome | 354,080 | Δ9 bp | coding (314-322/900 nt) | cynR← | transcriptional activator of cyn operon; autorepressor |
| E. coli genome | 407,471 | C→T | W156*(TGG→TAG) | araJ← | arabinose-inducible putative transporter, MFS family |
| E. coli genome | 829,599 | G→T | M358I(ATG→ATT) | dinG→ | ATP-dependent DNA helicase |
| E. coli genome | 1,104,830 | IS element integration | loss of function | opgG | osmoregulated periplasmic glucan (OPG) biosynthesis periplasmic protein |
| E. coli genome | 2,681,289 | C→A | D292Y(GAT→TAT) | glrR← | response regulator regulating glmY sRNA in two-component system with sensor protein GlrK |
| E. coli genome | 2,901,251 | C→A | G17V(GGT→GTT) | eno← | enolase |
| E. coli genome | 3,208,093 | T→C | F563S(TTC→TCC) | rpoD→ | RNA polymerase, sigma 70 (sigma D) factor |
| E. coli genome | 3,236,935 | C→T | G389D(GGT→GAT) | uxaC→ | uronate isomerase |
| E. coli genome | 3,433,439 | C→A | R317L(CGC→CTC) | rpoA→ | RNA polymerase, alpha subunit |
| E. coli genome | 3,547,518 | G→A | E359K(GAA→AAA) | malT→ | mal regulon transcriptional activator |
| E. coli genome | 3,729,347 | G→A | E337K(GAG→AAG) | xylR→ | xylose divergent operon transcriptional activator |
| E. coli genome | 4,173,770 | T→G | D866E(GAT→GAG) | rpoB→ | RNA polymerase, beta subunit |
| E. coli genome | 4,209,763-4,232,203 | large (22,441 bp) chromosomal deletion | | 17 genes: aceK, arpA, iclR, metH, yjbB, pepE, rluF, yjbD, lysC, pgi, yjbE, yjbF, yjbG, yjbH, yjbT, psiE, xylE | |
| E. coli genome | 4,275,144 | C→T | intergenic (−3/+197) | yjcH←/←acs | DUF485 family inner membrane protein/acetyl-CoA synthetase |

TABLE 7-continued

| | | mutations identified in evolved clone #4 | | | |
|---|---|---|---|---|---|
| chromosome | position | mutation | annotation | gene | description |
| *E. coli* genome | 4,276,215 | C→A | R362L(CGC→CTC) | acs← | acetyl-CoA synthetase |
| *E. coli* genome | 4,629,517 | C→T | V203M(GTG→ATG) | arcA← | response regulator in two-component regulatory system with ArcB or CpxA |
| pFDH plasmid | 901 | Δ5 bp | intergenic (−109/−106) | strepR←/ →pseudFDH | streptomycin resistance gene/formate dehydrogenase |

TABLE 8

| | | mutations identified in evolved clone #5 | | | |
|---|---|---|---|---|---|
| chromosome | position | mutation | annotation | gene | description |
| *E. coli* genome | 103,910 | (CTTCCAGGAC - SEQ ID NO: 9)1→2 | coding (867/918 nt) | lpxC→ | UDP-3-O-acyl N-acetylglucosamine deacetylase |
| *E. coli* genome | 155,132 | C→G | R161P(CGC→CCC) | pcnB← | poly(A) polymerase |
| *E. coli* genome | 354,080 | Δ9 bp | coding (314-322/900 nt) | cynR← | transcriptional activator of cyn operon; autorepressor |
| *E. coli* genome | 407,471 | C→T | W156*(TGG→TAG) | araJ← | arabinose-inducible putative transporter, MFS family |
| *E. coli* genome | 829,599 | G→T | M358I(ATG→ATT) | dinG→ | ATP-dependent DNA helicase |
| *E. coli* genome | 1,104,830 | IS element integration | | opgG | osmoregulated periplasmic glucan (OPG) biosynthesis periplasmic protein |
| *E. coli* genome | 1,660,340 | C→T | P257S(CCC→TCC) | clcB→ | H(+)/Cl(−) exchange transporter |
| *E. coli* genome | 2,681,289 | C→A | D292Y(GAT→TAT) | glrR← | response regulator regulating glmY sRNA in two-component system with sensor protein GlrK |
| *E. coli* genome | 2,901,251 | C→A | G17V(GGT→GTT) | eno← | enolase |
| *E. coli* genome | 3,208,093 | T→C | F563S(TTC→TCC) | rpoD→ | RNA polymerase, sigma 70 (sigma D) factor |
| *E. coli* genome | 3,433,439 | C→A | R317L(CGC→CTC) | rpoA← | RNA polymerase, alpha subunit |
| *E. coli* genome | 3,547,518 | G→A | E359K(GAA→AAA) | malT→ | mal regulon transcriptional activator |
| *E. coli* genome | 3,729,347 | G→A | E337K(GAG→AAG) | xylR→ | xylose divergent operon transcriptional activator |
| *E. coli* genome | 4,173,770 | T→G | D866E(GAT→GAG) | rpoB→ | RNA polymerase, beta subunit |
| *E. coli* genome | 4,209,763-4,232,203 | large (22,441 bp) chromosomal deletion | | 17 genes: aceK, arpA, iclR, metH, yjbB, pepE, rluF, yjbD, lysC, pgi, yjbE, yjbF, yjbG, yjbH, yjbT, psiE, xylE | |
| *E. coli* genome | 4,275,144 | C→T | intergenic (−3/+197) | yjcH←/←acs | DUF485 family inner membrane protein/acetyl-CoA synthetase |
| *E. coli* genome | 4,276,215 | C→A | R362L(CGC→CTC) | acs← | acetyl-CoA synthetase |
| *E. coli* genome | 4,629,517 | C→T | V203M(GTG→ATG) | arcA← | response regulator in two-component regulatory system with ArcB or CpxA |
| pFDH plasmid | 901 | Δ5 bp | intergenic (−109/−106) | strepR←/ →pseudFDH | streptomycin resistance gene/formate dehydrogenase |

TABLE 9

| | | | mutations identified in evolved clone #6 | | |
|---|---|---|---|---|---|
| chromosome | position | mutation | annotation | gene | description |
| *E. coli* genome | 130,787 | T→A | intergenic (+88/−88) | acnB→/ →yacL | bifunctional aconitate hydratase 2/2-methylisocitrate dehydratase/UPF0231 family protein |
| *E. coli* genome | 155,132 | C→G | R161P(CGC→CCC) | pcnB← | poly(A) polymerase |
| *E. coli* genome | 188,740 | C→G | I133M(ATC→ATG) | pyrH→ | uridylate kinase |
| *E. coli* genome | 407,471 | C→T | W156*(TGG→TAG) | araJ← | arabinose-inducible putative transporter, MFS family |

TABLE 9-continued

| | | | | | |
|---|---|---|---|---|---|
| | | | mutations identified in evolved clone #6 | | |
| chromosome | position | mutation | annotation | gene | description |
| E. coli genome | 567,750 | IS2(−) +5 bp | intergenic (+43/−70) | ybcM→/ →ylcH | DLP12 prophage; putative DNA-binding transcriptional regulator/uncharacterized protein, DLP12 prophage |
| E. coli genome | 1,147,311 | A→C | intergenic (+4/−84) | acpP→/ →fabF | acyl carrier protein (ACP)/3-oxoacyl-[acyl-carrier-protein] synthase II |
| E. coli genome | 1,256,820 | A→G | I171T(ATC→ACC) | prs← | phosphoribosylpyrophosphate synthase |
| E. coli genome | 1,783,016 | G→A | D109N(GAT→AAT) | aroH→ | 3-deoxy-D-arabino-heptulosonate-7-phosphate synthase, tryptophan repressible |
| E. coli genome | 3,208,093 | T→C | F563S(TTC→TCC) | rpoD→ | RNA polymerase, sigma 70 (sigma D) factor |
| E. coli genome | 3,547,518 | G→A | E359K(GAA→AAA) | malT→ | mal regulon transcriptional activator |
| E. coli genome | 3,729,347 | G→A | E337K(GAG→AAG) | xylR→ | xylose divergent operon transcriptional activator |
| E. coli genome | 4,173,770 | T→G | D866E(GAT→GAG) | rpoB→ | RNA polymerase, beta subunit |
| E. coli genome | 4,224,841 | C→T | H386Y(CAC→TAC) | pgi→ | glucosephosphate isomerase |
| pFDH plasmid | 918 | Δ8 bp | intergenic (−126/−86) | strepR←/ →pseudFDH | streptomycin resistance gene/formate dehydrogenase |

The first category consists of genes encoding enzymes with a direct metabolic link to the function of the Calvin cycle. In line with previous analysis showing the need to balance the flux branch (bifurcation) points from autocatalytic cycles to ensure stable biomass production (Barenholz et al., 2017), a mutation in prs (I171T) was found, the main flux branch point of the Calvin cycle in clone #6. This gene, which encodes ribose-phosphate-diphosphokinase, diverts ribose-phosphate towards biomass. Mutations in this enzyme were shown to play a crucial role in the kinetic stabilization of the Calvin cycle in E. coli by reducing the rate of D-ribose-5-phosphate efflux out of the cycle (Antonovsky et al., 2016; Herz et al., 2017). An additional key flux branch point is the gene pgi, encoding for glucosephosphate isomerase, whose inactivation was already shown to be important for stable operation of the synthetic Calvin cycle in a previous study (Herz et al., 2017). In some of the isolated autotrophic clones (#3-#5), the pgi gene is completely absent, along with 16 other genes as part of a large (≈22 kb) chromosomal deletion. In the remaining clones, a single point mutation (H386Y, clones #1, #2 and #6) was identified in one of the catalytic residues at the active site (Totir et al., 2012), likely leading to the deactivation of the enzyme. Overall, the deactivation of Pgi, either by gene deletion or active site mutation, is common to all autotrophic clones isolated from the chemostat. Beyond these two previously reported flux branch points, mutations in genes of two additional flux branch points were observed. The first is aroH (mutation D109N in clones #1 & #6; and A68E, in clone #2), which encodes a 2-dehydro-3-deoxyphosphoheptonate aldolase, the first committing step in the chorismate pathway leading to the biosynthesis of aromatic amino acids from erythrose-4-phosphate and phosphoenolpyruvate. All the clones without a mutated aroH gene contain a mutation in the enolase-encoding eno gene (G17V, clones #3-#5), which could also be considered an extension of a bifurcation point affecting the flux diverted off the Calvin cycle. Overall, all the autotrophic isolated clones had mutations in more than one flux branch point, consistent with the mutations required for the stabilization of the Calvin cycle in E. coli (Antonovsky et al., 2016; Herz et al., 2017). Within the energy module, either an 8-base-pair or a 5-base-pair deletion was observed in the promoter region of the plasmid-encoded fdh gene. This could affect the expression level of FDH so as to tune the rate of NADH production with the reducing power consumption rate by the Calvin cycle. The fact that two independent mutations were observed occuring in the same promoter region of fdh suggests a functional role for these mutations. However, FDH activity assays of crude extracts of WT E. coli BW25113 transformed with the mutated (8-base-pair deletion variant) and non-mutated plasmids showed no significant difference in activity.

A second category of mutated genes consists of those commonly observed to be mutated in previous adaptive laboratory evolution experiments (Phaneuf et al., 2019). Members of this group include pcnB (R161P) (Masters et al., 1993), rpoB (D866E) (Utrilla et al., 2016), rpoD (F563S) (Malhotra, Severinova and Darst, 1996), malT (E359K) (Gresham and Hong, 2015), and araJ (W156*) (Reeder and Schleif, 1991). These mutations are suggested to be attributed to generic selective pressures found in long-term lab evolution experiments in minimal media, and not to be specifically geared for the autotrophic phenotype. Similarly, the mutation in the xylR gene (Song and Park, 1997), encoding the regulatory protein for operons responsible for the catabolism of the sugar D-xylose (E337K), is probably related to the long period of xylose starvation in the chemostat, but is irrelevant under the final autotrophic growth conditions. This is in line with observed mutations in the xylose catabolism operon in previous evolution experiments conducted in xylose-limited chemostats that were found to be not essential for the phenotype of the evolved strain (Antonovsky et al., 2016; Herz et al., 2017). Further supporting the notion that the above mentioned mutations are generic mutations common to adaptive laboratory evolution experiments, all of them were fixed in the entire chemostat population during the first 130 days of the evolution, long before the appearance of the autotrophic phenotype. Therefore, they are most likely connected to the starvation state in which the cells were present during the evolution rather than directly related to the autotrophic phenotype. Nevertheless, some of these mutations might be linked to the emergence of the autotrophic phenotype through their global regulatory functions, such as in the case of the core transcription machinery (rpoB/rpoD). In addition, mutations in pcnB, which encodes poly(A) polymerase I, were reported to decrease the copy number of ColE1 plasmids (Masters et al., 1993; Pontrelli, Fricke, et al., 2018). Since pFDH has a ColE1 origin of replication, the pcnB mutation most likely reduces the copy number of this plasmid to decrease the cellular burden associated with its maintenance and gene expression.

The last category of mutated genes includes mutations that currently have no characterized role.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated in its/their entirety.

REFERENCES

Aigner, H. et al. (2017) 'Plant RuBisCo assembly in *E. coli* with five chloroplast chaperones including BSD2', *Science*, 358(6368), pp. 1272-1278.

Antonovsky, N. et al. (2016) 'Sugar Synthesis from $CO_2$ in *Escherichia coli*', *Cell*, 166(1), pp. 1-11.

Baba, T. et al. (2006) 'Construction of *Escherichia coli* K-12 in-frame, single-gene knockout mutants: the Keio collection', *Molecular systems biology*. EMBO Press, 2(1), p. 2006.0008.

Barenholz, U. et al. (2017) 'Design principles of autocatalytic cycles constrain enzyme kinetics and force low substrate saturation at flux branch points', *eLife*. eLife Sciences Publications Limited, 6, p. e20667.

Bar-On, Y. M., Phillips, R. and Milo, R. (2018) 'The biomass distribution on Earth', *Proceedings of the National Academy of Sciences of the United States of America*, 115(25), pp. 6506-6511.

Barrick, J. E. et al. (2014) 'Identifying structural variation in haploid microbial genomes from short-read resequencing data using breseq', *BMC genomics*, 15, p. 1039.

Bennett, B. D. et al. (2008) 'Absolute quantitation of intracellular metabolite concentrations by an isotope ratio-based approach', *Nature protocols*, 3(8), pp. 1299-1311.

Berrios-Rivera, S. J., Bennett, G. N. and San, K. -Y. (2002) 'Metabolic Engineering of *Escherichia coli*: Increase of NADH Availability by Overexpressing an NAD p -Dependent Formate Dehydrogenase', *Metabolic engineering*, 229, pp. 217-229.

Blount, Z. D. et al. (2012) 'Genomic analysis of a key innovation in an experimental *Escherichia coli* population', *Nature*, 489(7417), pp. 513-518.

von Borzyskowski, L. S. et al. (2018) 'An engineered Calvin-Benson-Bassham cycle for carbon dioxide fixation in Methylobacterium extorquens AM1', *Metabolic engineering*. Elsevier Inc., 47(July 2017), pp. 423-433.

Braatsch, S. et al. (2008) '*Escherichia coli* strains with promoter libraries constructed by Red/ET recombination pave the way for transcriptional fine-tuning', *BioTechniques*, 45(3), pp. 335-337.

Cherepanov, P. P. and Wackernagel, W. (1995) 'Gene disruption in *Escherichia coli*: TcR and KmR cassettes with the option of Flp-catalyzed excision of the antibiotic-resistance determinant', *Gene*, 158(1), pp. 9-14.

Claassens, N. J. et al. (2018) 'Towards sustainable feedstocks: A guide to electron donors for microbial carbon fixation', *Current opinion in biotechnology*, 50, pp. 195-205.

Clasquin, M. F., Melamud, E. and Rabinowitz, J. D. (2012) 'LC-MS data processing with MAVEN: a metabolomic analysis and visualization engine', *Current protocols in bioinformatics/editoral board, Andreas D. Baxevanis . . . [et al.]*. Wiley Online Library, 37(1), pp. 14-11.

Crowther, T. W. et al. (2015) 'Mapping tree density at a global scale', *Nature*, 525(7568), pp. 201-205.

Ebrahim, A., Lerman, J. A., Pals son, B. O. and Hyduke, D. R., (2013) 'COBRApy: constraints-based reconstruction and analysis for python'. BMC systems biology, 7(1), p. 74.

Egorov, A. M. et al. (1980) 'Kinetic and structural properties of Nad-Dependent bacterial formate dehydrogenase', *Journal of Solid-Phase Biochemistry*, 5(1), pp. 19-33.

Folsom, J. P. and Carlson, R. P. (2015) 'Physiological, biomass elemental composition and proteomic analyses of *Escherichia coli* ammonium-limited chemostat growth, and comparison with iron- and glucose-limited chemostat growth', *Microbiology*, 161(8), pp. 1659-1670.

French, K. E. (2019) 'Harnessing synthetic biology for sustainable development', *Nature Sustainability*. Nature Publishing Group, 2(4), pp. 250-252.

Glazyrina, J. et al. (2010) 'High cell density cultivation and recombinant protein production with *Escherichia coli* in a rocking-motion-type bioreactor', *Microbial cell factories*, 9, p. 42.

Grenier, F. et al. (2014) 'Complete Genome Sequence of *Escherichia coli* BW25113', *Genome announcements*, 2(5). doi: 10.1128/genomeA.01038-14.

Gresham, D. and Hong, J. (2015) 'The functional basis of adaptive evolution in chemostats', *FEMS microbiology reviews*, 39(1), pp. 2-16.

Grunwald, S. et al. (2015) 'Kinetic and stoichiometric characterization of organoautotrophic growth of *Ralstonia eutropha* on formic acid in fed-batch and continuous cultures', *Microbial biotechnology*, 8(1), pp. 155-163.

Herz, E. et al. (2017) 'The genetic basis for the adaptation of *E. coli* to sugar synthesis from CO2', *Nature communications*. Springer US. doi: 10.1038/s41467-017-01835-3.

Holzhütter, H. G., (2004) 'The principle of flux minimization and its application to estimate stationary fluxes in metabolic networks'. *European journal of biochemistry*, 271(14), pp.2905-2922.

Huang, H. et al. (2012) 'Electron bifurcation involved in the energy metabolism of the acetogenic bacterium Moorella thermoacetica growing on glucose or H2 plus CO2', *Journal of bacteriology*, 194(14), pp. 3689-3699.

Innocent, B. et al. (2009) 'Electro-reduction of carbon dioxide to formate on lead electrode in aqueous medium', *Journal of Applied Electrochemistry*. Springer Netherlands, 39(2), pp. 227-232.

Keller, M. W. et al. (2013) 'Exploiting microbial hyperthermophilicity to produce an industrial chemical, using hydrogen and carbon dioxide', *Proceedings of the National Academy of Sciences of the United States of America*, 110(15), pp. 5840-5845.

Kromdijk, J. et al. (2016) 'Improving photosynthesis and crop productivity by accelerating recovery from photoprotection', *Science*, 354(6314), pp. 857-861.

Kubis, A. and Bar-Even, A. (2019) 'Synthetic biology approaches for improving photosynthesis', *Journal of experimental botany*, 70(5), pp. 1425-1433.

Malhotra, A., Severinova, E. and Darst, S. A. (1996) 'Crystal Structure of a 670 Subunit Fragment from *E. coli* RNA Polymerase', *Cell,* 87(1), pp. 127-136.

Marlière, P. et al. (2011) 'Chemical evolution of a bacterium's genome', *Angewandte Chemie,* 50(31), pp. 7109-7114.

Masters, M. et al. (1993) 'The pcnB gene of *Escherichia coli,* which is required for ColE1 copy number maintenance, is dispensable', *Journal of bacteriology,* 175(14), pp. 4405-4413.

Mattozzi, M. D. et al. (2013) 'Expression of the sub-pathways of the *Chloroflexus aurantiacus* 3-hydroxypropionate carbon fixation bicycle in *E. coli*: Toward horizontal transfer of autotrophic growth', *Metabolic engineering.* Elsevier, 16, pp. 130-139.

Nielsen, J. and Keasling, J. D. (2016) 'Engineering Cellular Metabolism', *Cell.* Elsevier Ltd, 164(6), pp. 1185-1197.

Ort, D. R. et al. (2015) 'Redesigning photosynthesis to sustainably meet global food and bioenergy demand', *Proceedings of the National Academy of Sciences of the United States of America,* 112(28), pp. 8529-8536.

Orth, J. D., Fleming, R. M. and Palsson, B. O., (2010) 'Reconstruction and use of microbial metabolic networks: the core *Escherichia coli* metabolic model as an educational guide'. *EcoSal plus.*

Orth, J. D., Thiele, I. and Palsson, B. Ø. (2010) 'What is flux balance analysis?', *Nature biotechnology.* Nature Publishing Group, 28, p. 245.

Phaneuf, P. V. et al. (2019) 'ALEdb 1.0: a database of mutations from adaptive laboratory evolution experimentation', *Nucleic Acids Research,* pp. D1164-D1171. doi: 10.1093/nar/gky983.

Pontrelli, S., Fricke, R. C. B., et al. (2018) 'Directed strain evolution restructures metabolism for 1-butanol production in minimal media', *Metabolic engineering,* 49, pp. 153-163.

Pontrelli, S., Chiu, T. -Y., et al. (2018) '*Escherichia coli* as a host for metabolic engineering', *Metabolic engineering,* 50, pp. 16-46.

Popov, V. O. and Lamzin, V. S. (1994) 'NAD(+)-dependent formate dehydrogenase', *Biochemical Journal,* 301 (Pt 3), pp. 625-643.

Pronk, J. T. et al. (1991) 'Growth of *Thiobacillus ferrooxidans* on Formic Acid', *Applied and environmental microbiology,* 57(7), pp. 2057-2062.

Quandt, E. M. et al. (2014) 'Recursive genomewide recombination and sequencing reveals a key refinement step in the evolution of a metabolic innovation in *Escherichia coli*', *Proceedings of the National Academy of Sciences of the United States of America,* 111(6), pp. 2217-2222.

Reeder, T. and Schleif, R. (1991) 'Mapping, sequence, and apparent lack of function of araJ, a gene of the *Escherichia coli* arabinose regulon', *Journal of bacteriology,* 173(24), pp. 7765-7771.

Sauer, U. (2001) 'Evolutionary engineering of industrially important microbial phenotypes', *Advances in biochemical engineering/biotechnology,* 73, pp. 129-169.

Schwander, T. et al. (2016) 'A synthetic pathway for the fixation of carbon dioxide in vitro', *Science,* 354(6314). doi: 10.1126/science.aah5237.

Smith, A. M. and Stitt, M. (2007) 'Coordination of carbon supply and plant growth', *Plant, cell & environment,* 30(9), pp. 1126-1149.

Sonderegger, M. and Sauer, U. (2003) 'Evolutionary Engineering of *Saccharomyces cerevisiae* for Anaerobic Growth on Xylose', *Applied and environmental microbiology,* 69(4), pp. 1990-1998.

Song, S. and Park, C. (1997) 'Organization and regulation of the D-xylose operons in *Escherichia coli* K-12: Xy1R acts as a transcriptional activator', *Journal of bacteriology,* 179(22), pp. 7025-7032.

South, P. F. et al. (2019) 'Synthetic glycolate metabolism pathways stimulate crop growth and productivity in the field', *Science,* 363(6422). doi: 10.1126/science.aat9077.

Thomason, L. C., Costantino, N. and Court, D. L. (2007) '*E. coli* genome manipulation by P1 transduction', *Current protocols in molecular biology*/edited by Frederick M. Ausubel . . . [et al.], Chapter 1, p. Unit 1.17.

Totir, M. et al. (2012) 'Macro-to-micro structural proteomics: native source proteins for high-throughput crystallization', *PloS one,* 7(2), p. e32498.

Utrilla, J. et al. (2016) 'Global Rebalancing of Cellular Resources by Pleiotropic Point Mutations Illustrates a Multi-scale Mechanism of Adaptive Evolution', *Cell systems,* 2(4), pp. 260-271.

Volpers, M. et al. (2016) 'Integrated In Silico Analysis of Pathway Designs for Synthetic Photo-Electro-Autotrophy', *PloS one,* 11(6), p. e0157851.

Wides, A. and Milo, R. (2018) 'Understanding the Dynamics and Optimizing the Performance of Chemostat Selection Experiments', arXiv [q-bio.PE]. Available at: www(dot)arxiv(dot)org/abs/1806(dot)00272.

Yishai, O. et al. (2016) 'The formate bio-economy', *Current Opinion in Chemical Biology,* pp. 1-9. doi: 10.1016/j.cbpa.2016.07.005.

Zamboni, N. and Sauer, U. (2009) 'Novel biological insights through metabolomics and 13C-flux analysis', *Current opinion in microbiology,* 12(5), pp. 553-558.

Zelcbuch, L. et al. (2013) 'Spanning high-dimensional expression space using ribosome-binding site combinatorics', *Nucleic acids research,* 41(9), p. e98.

What is claimed is:

1. A population of recombinant bacteria which is genetically modified to express formate dehydrogenase (FDH), phosphoribulokinase (prk) and Ribulose-Bisphosphate Carboxylase/oxygenase (RuBisCo), wherein the recombinant bacteria is *E. Coli*, wherein the bacteria is capable of autotrophic growth following a culturing protocol which comprises:

(a) culturing said bacteria in a medium comprising a pentose or hexose sugar;

and subsequently (b) reducing the amount of said pentose or hexose sugar in said medium and increasing the amount of formate in said medium.

2. The population of recombinant bacteria of claim 1, being further genetically modified to express carbonic anhydrase (CA).

3. The population of recombinant bacteria of claim 1, wherein said bacteria is modified so as to delete 6-phosphate-1-dehydrogenase (zwf), phosphofructokinase A (pfkA) and phosphofructokinase B (pfkB).

4. The population of recombinant bacteria of claim 1, (a) wherein glucosephosphate isomerase (pgi) of said bacteria comprises a H386Y mutation;

(b) wherein phosphoribosylpyrophosphate synthase (prs) of said bacteria comprises a I171T mutation;

(c) wherein uridylate kinase (pyrH) of the bacteria comprises a I133M mutation; and/or (d) wherein 3-deoxy-D-arabino-heptulosonate-7-phosphate synthase (aroH) of said bacteria comprises D109N mutation.

5. The population of recombinant bacteria of claim 1, having a D866E mutation in RNA polymerase, beta subunit (rpoB).

6. The population of recombinant bacteria of claim 1, being an autotroph.

7. The population of recombinant bacteria of claim 1, wherein the bacteria is not, in its native state, capable of biosynthesizing metabolites by utilizing $CO_2$ as a sole carbon source.

8. A cell culture comprising a medium and the population of recombinant bacteria of claim 1, wherein said medium comprises formate.

9. The cell culture of claim 8, being devoid of an additional organic carbon source.

* * * * *

SEQUENCE LISTING

<160> NUMBER OF SEQ ID NOS: 9

<210> SEQ ID NO 1
<211> LENGTH: 1422
<212> TYPE: DNA
<213> ORGANISM: Rhodospirillum rubrum

<400> SEQUENCE: 1
atgcatcatc accatcacca catggaccag tcatctcgtt acgtcaatct ggcgctcaag      60
gaagaggatc tgatcgccgg cggcgagcat gtgctttgtg cctatatcat gaagcccaag     120
gccggatatg gctatgtggc gaccgcggcg catttcgccg ccgagagttc gacgggcacc     180

-continued

```
aacgtcgagg tctgcaccac cgacgatttc acccggggcg tcgacgccct ggtctatgag      240
gtggacgagg cccgcgagct gaccaagatc gcctatccgg tggctttgtt cgaccgcaac      300
atcaccgacg gcaaggcgat gatcgcctcg ttcctgacgc tcaccatggg aaacaaccag      360
ggtatgggcg acgtggaata cgccaagatg cacgatttct atgtgcccga ggcttatcgc      420
gccctgtttg atggcccgag cgtcaatatc tcggccctgt ggaaagtgct ggggcggccc      480
gaggtcgacg gcggtctggt cgtcggcacg atcatcaagc cgaagctcgg cctgcgtccc      540
aagcccttcg ccgaggcctg ccacgccttc tggctgggcg cgacttcat caagaacgac      600 gagccccagg gcaatcagcc cttcgccccc ttgcgcgaca ccatcgccct ggtcgccgac      660
gccatgaggc gggcccagga cgagaccggc gaggccaagc tgttctcggc caatatcacc      720
gccgacgatc ccttcgagat catcgcccgt ggcgagtatg tgctggagac cttcggcgag      780
aacgcctcgc atgtcgcctt gctggtcgac ggctatgtcg ccggcgccgc ggcgatcacc      840
acggcgcgcc gccgcttccc cgataacttc ttgcattatc accgggctgg ccacggcgcc      900
gtcacctcgc cccagtccaa gcgcggctat accgccttcg tccattgcaa gatggcccgc      960
cttcaaggcg ccagcggcat ccacaccggc accatgggct ttggcaagat ggaaggcgag     1020
tccagcgacc gcgccatcgc ctatatgctg acccaggacg aggcccaggg gccgttctac     1080
cgtcaatcct ggggcggcat gaaggcttgt acgccgatca tcagcggcgg catgaacgcc     1140
ctgcgcatgc ccggcttctt cgagaacctg ggtaatgcca atgtcatctt gaccgccggc     1200
ggcggcgcct tcggccatat cgacggcccg gtggccgggg cgcggtcgtt gcgtcaagcc     1260
tggcaagcct ggcgggacgg ggttccggtt ctggactatg cccgcgagca caaggaactg     1320 gccccgcgcct tcgagtcctt ccccggcgac gccgaccaga tctatccggg ctggcgcaag     1380
gccctgggcg tcgaggacac ccgcagcgcc cttccggcgt aa                        1422
```

<210> SEQ ID NO 2
<211> LENGTH: 1020
<212> TYPE: DNA
<213> ORGANISM: Synechococcus

<400> SEQUENCE: 2

```
atgcatcatc accatcacca cagcaagcca gatcgtgttg ttttgatcgg cgttgccggt       60
gactccggtt gcggcaaatc aaccttccta aatcgccttg ccgacttgtt tggtacggaa      120
ttgatgacgg tcatctgctt ggatgactat cacagtctcg atcgcaaggg ccggaaggaa      180
gcaggcgtaa cggctttgga tccccgcgcc aacaactttg acttgatgta tgaacaggtc      240
aaggcgttga agaacggcga aacgatcatg aagccgatct acaaccatga aaccggcttg      300
atcgatccgc ccgaaaaaat cgaacccaat cgcatcattg tgatcgaggg tctgcatccg      360
ctttacgacg agcgcgtgcg tgaactgctc gatttcagcg tttacctcga catcgatgac      420
gaagtcaaaa tcgcttggaa gatccaacgc gatatggcag aacgcggcca ctcctacgaa      480
gatgtcctcg cctcgatcga agcgcgccgc cctgacttca aggcctacat tgagccccag      540
cgtggccatg cggacatcgt catccgcgtc atgccgaccc agctaatccc caatgacacc      600
gagcgcaagg tgctgcgggt gcagttgatc caacgggaag gccgcgatgg ttttgagccg      660
gcttacctgt tcgacgaagg ttcgaccatc cagtggacgc cctgcggtcg taagctgacc      720
tgctcctatc cggcattcg cttagcctac ggccctgaca cctactacgg tcacgaagtc      780
tcagtgcttg aggtcgacgg tcagttcgag aacctcgaag agatgatcta cgtcgagggc      840
```

-continued

```
cacctcagca agaccgacac gcagtactac ggtgagttga cccacctgct gctacagcac      900
aaagattacc cgggttcgaa caacggcacg ggtctgttcc aagtgctgac cggcctgaaa      960
atgcgggcgg cctatgagcg tttgacctcc caagcagcac ccgtcgccgc tagtgtctag     1020

<210> SEQ ID NO 3
<211> LENGTH: 660
<212> TYPE: DNA
<213> ORGANISM: Rhodospirillum rubrum

<400> SEQUENCE: 3
atgcatcatc accatcacca cgacatccag gatctcatta ccaacaatcg gaaatgggcc       60
gaggagcgcg aatccgccct tcctggctat tttcatatcc tcagcgaagt gcagtcgccg      120 aagttttttgt ggatcggctg ctcggactcg cgggtgccgg ccaatgaaat cgtcggcatg      180
cagccgggcg aacttttcgt tcaccgcaac atcgccaacg ttgttcccca tgccgacgcc      240
aattgccacg ccgtgctcga atacgccatc gacgtgctga aggtcgagca catcatggtc      300
gtcggccatt acggctgcgg cggggttcgc gccgccctga accgtctggc catggggccg      360
atcgacaact ggctgtccca catcaaggac atcgcccgta tcttcgccgc cgagctggaa      420
gacctacccg acgaggaaag ccgggtcgac cggctgtgcg aactcaacgc catggcccag      480
gtgatgaacg tggcgcgcac ctcgatggtt caggcggctt ggcgacgcgg ccagcctttg      540
gccatccacg cttggtgcta tggtctgaag actgggctgg tcaatgatct tggccgaacc      600
ctaacccgca tcgccgatct gcccgaaccc tatcggctga tctttcccga tcaggtctaa      660

<210> SEQ ID NO 4
<211> LENGTH: 1224
<212> TYPE: DNA
<213> ORGANISM: Pseudomonas sp. 101

<400> SEQUENCE: 4
atgcatcatc accatcacca cgctaaagtt ctgtgcgttc tgtacgacga cccggttgac       60
ggttacccga aaacctacgc tcgtgacgac ctgccgaaaa tcgaccacta cccgggtggt      120
cagaccctgc cgaccccgaa agctatcgac ttcaccccgg gtcagctgct gggttctgtt      180
tctggtgaac tgggtctgcg taaatacctg gaatctaacg gtcacaccct ggttgttacc      240
tctgacaaag acggtccgga ctctgttttc gaacgtgaac tggttgacgc tgacgttgtt      300
atctctcagc cgttctggcc ggcttacctg accccggaac gtatcgctaa agctaaaaac      360
ctgaaactgg ctctgaccgc tggtatcggt tctgaccacg ttgacctgca atctgctatc      420
gaccgtaacg ttaccgttgc tgaagttacc tactgcaact ctatctctgt tgctgaacac      480
gttgttatga tgatcctgtc tctggttcgt aactacctgc cgtctcacga atgggctcgt      540
aaaggtggtt ggaacatagc tgactgcgta agccacgctt acgacctgga agctatgcac      600
gttggtaccg ttgctgctgg tcgtatcggt ctggctgttc tgcgtcgtct ggctccgttc      660
gacgttcacc tgcactacac cgaccgtcac cgtctgccgg aatctgttga aaaagaactg      720
aacctgacct ggcacgctac ccgtgaagac atgtacccgg tttgcgacgt tgttaccctg      780
aactgcccgc tgcacccgga aaccgaacac atgatcaacg acgaaaccct gaaactgttc      840
aaacgtggtg cttacatcgt taacaccgct cgtggtaaac tgtgcgaccg tgacgctgtt      900
gctcgtgctc tggaatctgg tcgtctggct ggttatgcgg gtgacgtgtg gttccccag      960 ccggctccga aagaccaccc gtggcgtacc atgccgtaca acggtatgac cccgcacatc     1020
tctggtacca ccctgaccgc tcaggctcgt tacgctgctg gtaccgtga aatcctggaa     1080
```

-continued

```
tgcttcttcg aaggtcgtcc gatccgtgac gaatacctga tcgttcaggg tggtgctctg      1140
gctggtaccg tgctcactc ttactctaaa ggtaacgcta ccggtggttc tgaagaagct      1200
gctaaattca aaaaagctgt ttaa                                              1224
```

<210> SEQ ID NO 5
<211> LENGTH: 473
<212> TYPE: PRT
<213> ORGANISM: Rhodospirillum rubrum

<400> SEQUENCE: 5

```
Met His His His His His His Met Asp Gln Ser Ser Arg Tyr Val Asn
1               5                   10                  15

Leu Ala Leu Lys Glu Glu Asp Leu Ile Ala Gly Gly Glu His Val Leu
            20                  25                  30

Cys Ala Tyr Ile Met Lys Pro Lys Ala Gly Tyr Gly Tyr Val Ala Thr
            35                  40                  45

Ala Ala His Phe Ala Ala Glu Ser Ser Thr Gly Thr Asn Val Glu Val
        50                  55                  60

Cys Thr Thr Asp Asp Phe Thr Arg Gly Val Asp Ala Leu Val Tyr Glu
65                  70                  75                  80

Val Asp Glu Ala Arg Glu Leu Thr Lys Ile Ala Tyr Pro Val Ala Leu
                85                  90                  95

Phe Asp Arg Asn Ile Thr Asp Gly Lys Ala Met Ile Ala Ser Phe Leu
                100                 105                 110

Thr Leu Thr Met Gly Asn Asn Gln Gly Met Gly Asp Val Glu Tyr Ala
            115                 120                 125

Lys Met His Asp Phe Tyr Val Pro Glu Ala Tyr Arg Ala Leu Phe Asp
        130                 135                 140

Gly Pro Ser Val Asn Ile Ser Ala Leu Trp Lys Val Leu Gly Arg Pro
145                 150                 155                 160

Glu Val Asp Gly Gly Leu Val Val Gly Thr Ile Ile Lys Pro Lys Leu
                165                 170                 175

Gly Leu Arg Pro Lys Pro Phe Ala Glu Ala Cys His Ala Phe Trp Leu
            180                 185                 190

Gly Gly Asp Phe Ile Lys Asn Asp Glu Pro Gln Gly Asn Gln Pro Phe
            195                 200                 205

Ala Pro Leu Arg Asp Thr Ile Ala Leu Val Ala Asp Ala Met Arg Arg
        210                 215                 220

Ala Gln Asp Glu Thr Gly Glu Ala Lys Leu Phe Ser Ala Asn Ile Thr
225                 230                 235                 240

Ala Asp Asp Pro Phe Glu Ile Ile Ala Arg Gly Glu Tyr Val Leu Glu
                245                 250                 255

Thr Phe Gly Glu Asn Ala Ser His Val Ala Leu Leu Val Asp Gly Tyr
            260                 265                 270

Val Ala Gly Ala Ala Ala Ile Thr Thr Ala Arg Arg Arg Phe Pro Asp
        275                 280                 285

Asn Phe Leu His Tyr His Arg Ala Gly His Gly Ala Val Thr Ser Pro
    290                 295                 300

Gln Ser Lys Arg Gly Tyr Thr Ala Phe Val His Cys Lys Met Ala Arg
305                 310                 315                 320

Leu Gln Gly Ala Ser Gly Ile His Thr Gly Thr Met Gly Phe Gly Lys
            325                 330                 335

Met Glu Gly Glu Ser Ser Asp Arg Ala Ile Ala Tyr Met Leu Thr Gln
```

```
                  340              345              350

Asp Glu Ala Gln Gly Pro Phe Tyr Arg Gln Ser Trp Gly Gly Met Lys
        355              360              365

Ala Cys Thr Pro Ile Ile Ser Gly Gly Met Asn Ala Leu Arg Met Pro
    370              375              380

Gly Phe Phe Glu Asn Leu Gly Asn Ala Asn Val Ile Leu Thr Ala Gly
385              390              395              400

Gly Gly Ala Phe Gly His Ile Asp Gly Pro Val Ala Gly Ala Arg Ser
            405              410              415

Leu Arg Gln Ala Trp Gln Ala Trp Arg Asp Gly Val Pro Val Leu Asp
        420              425              430

Tyr Ala Arg Glu His Lys Glu Leu Ala Arg Ala Phe Glu Ser Phe Pro
        435              440              445

Gly Asp Ala Asp Gln Ile Tyr Pro Gly Trp Arg Lys Ala Leu Gly Val
    450              455              460

Glu Asp Thr Arg Ser Ala Leu Pro Ala
465              470

<210> SEQ ID NO 6
<211> LENGTH: 339
<212> TYPE: PRT
<213> ORGANISM: Synechococcus

<400> SEQUENCE: 6

Met His His His His His Ser Lys Pro Asp Arg Val Val Leu Ile
1               5               10              15

Gly Val Ala Gly Asp Ser Gly Cys Gly Lys Ser Thr Phe Leu Asn Arg
            20              25              30

Leu Ala Asp Leu Phe Gly Thr Glu Leu Met Thr Val Ile Cys Leu Asp
        35              40              45

Asp Tyr His Ser Leu Asp Arg Lys Gly Arg Lys Glu Ala Gly Val Thr
    50              55              60

Ala Leu Asp Pro Arg Ala Asn Asn Phe Asp Leu Met Tyr Glu Gln Val
65              70              75              80

Lys Ala Leu Lys Asn Gly Glu Thr Ile Met Lys Pro Ile Tyr Asn His
            85              90              95

Glu Thr Gly Leu Ile Asp Pro Pro Glu Lys Ile Glu Pro Asn Arg Ile
            100             105             110

Ile Val Ile Glu Gly Leu His Pro Leu Tyr Asp Glu Arg Val Arg Glu
        115             120             125

Leu Leu Asp Phe Ser Val Tyr Leu Asp Ile Asp Asp Glu Val Lys Ile
    130             135             140

Ala Trp Lys Ile Gln Arg Asp Met Ala Glu Arg Gly His Ser Tyr Glu
145             150             155             160

Asp Val Leu Ala Ser Ile Glu Ala Arg Arg Pro Asp Phe Lys Ala Tyr
            165             170             175

Ile Glu Pro Gln Arg Gly His Ala Asp Ile Val Ile Arg Val Met Pro
        180             185             190

Thr Gln Leu Ile Pro Asn Asp Thr Glu Arg Lys Val Leu Arg Val Gln
        195             200             205

Leu Ile Gln Arg Glu Gly Arg Asp Gly Phe Glu Pro Ala Tyr Leu Phe
    210             215             220

Asp Glu Gly Ser Thr Ile Gln Trp Thr Pro Cys Gly Arg Lys Leu Thr
225             230             235             240
```

-continued

```
Cys Ser Tyr Pro Gly Ile Arg Leu Ala Tyr Gly Pro Asp Thr Tyr Tyr
                245                 250                 255

Gly His Glu Val Ser Val Leu Glu Val Asp Gly Gln Phe Glu Asn Leu
            260                 265                 270

Glu Glu Met Ile Tyr Val Glu Gly His Leu Ser Lys Thr Asp Thr Gln
            275                 280                 285

Tyr Tyr Gly Glu Leu Thr His Leu Leu Leu Gln His Lys Asp Tyr Pro
        290                 295                 300

Gly Ser Asn Asn Gly Thr Gly Leu Phe Gln Val Leu Thr Gly Leu Lys
305                 310                 315                 320

Met Arg Ala Ala Tyr Glu Arg Leu Thr Ser Gln Ala Ala Pro Val Ala
                325                 330                 335

Ala Ser Val

<210> SEQ ID NO 7
<211> LENGTH: 219
<212> TYPE: PRT
<213> ORGANISM: Rhodospirillum rubrum

<400> SEQUENCE: 7

Met His His His His His His Asp Ile Gln Asp Leu Ile Thr Asn Asn
1               5                   10                  15

Arg Lys Trp Ala Glu Glu Arg Glu Ser Ala Leu Pro Gly Tyr Phe His
            20                  25                  30

Ile Leu Ser Glu Val Gln Ser Pro Lys Phe Leu Trp Ile Gly Cys Ser
        35                  40                  45

Asp Ser Arg Val Pro Ala Asn Glu Ile Val Gly Met Gln Pro Gly Glu
    50                  55                  60

Leu Phe Val His Arg Asn Ile Ala Asn Val Val Pro His Ala Asp Ala
65                  70                  75                  80

Asn Cys His Ala Val Leu Glu Tyr Ala Ile Asp Val Leu Lys Val Glu
                85                  90                  95

His Ile Met Val Val Gly His Tyr Gly Cys Gly Gly Val Arg Ala Ala
            100                 105                 110

Leu Asn Arg Leu Ala Met Gly Pro Ile Asp Asn Trp Leu Ser His Ile
            115                 120                 125

Lys Asp Ile Ala Arg Ile Phe Ala Ala Glu Leu Glu Asp Leu Pro Asp
    130                 135                 140

Glu Glu Ser Arg Val Asp Arg Leu Cys Glu Leu Asn Ala Met Ala Gln
145                 150                 155                 160

Val Met Asn Val Ala Arg Thr Ser Met Val Gln Ala Ala Trp Arg Arg
                165                 170                 175

Gly Gln Pro Leu Ala Ile His Ala Trp Cys Tyr Gly Leu Lys Thr Gly
            180                 185                 190

Leu Val Asn Asp Leu Gly Arg Thr Leu Thr Arg Ile Ala Asp Leu Pro
            195                 200                 205

Glu Pro Tyr Arg Leu Ile Phe Pro Asp Gln Val
    210                 215

<210> SEQ ID NO 8
<211> LENGTH: 407
<212> TYPE: PRT
<213> ORGANISM: Pseudomonas sp. 101

<400> SEQUENCE: 8

Met His His His His His His Ala Lys Val Leu Cys Val Leu Tyr Asp
```

```
1               5               10              15

Asp Pro Val Asp Gly Tyr Pro Lys Thr Tyr Ala Arg Asp Asp Leu Pro
            20              25              30

Lys Ile Asp His Tyr Pro Gly Gly Gln Thr Leu Pro Thr Pro Lys Ala
            35              40              45

Ile Asp Phe Thr Pro Gly Gln Leu Leu Gly Ser Val Ser Gly Glu Leu
        50              55              60

Gly Leu Arg Lys Tyr Leu Glu Ser Asn Gly His Thr Leu Val Val Thr
65              70              75              80

Ser Asp Lys Asp Gly Pro Asp Ser Val Phe Glu Arg Glu Leu Val Asp
                85              90              95

Ala Asp Val Val Ile Ser Gln Pro Phe Trp Pro Ala Tyr Leu Thr Pro
            100             105             110

Glu Arg Ile Ala Lys Ala Lys Asn Leu Lys Leu Ala Leu Thr Ala Gly
            115             120             125

Ile Gly Ser Asp His Val Asp Leu Gln Ser Ala Ile Asp Arg Asn Val
        130             135             140

Thr Val Ala Glu Val Thr Tyr Cys Asn Ser Ile Ser Val Ala Glu His
145             150             155             160

Val Val Met Met Ile Leu Ser Leu Val Arg Asn Tyr Leu Pro Ser His
                165             170             175

Glu Trp Ala Arg Lys Gly Gly Trp Asn Ile Ala Asp Cys Val Ser His
            180             185             190

Ala Tyr Asp Leu Glu Ala Met His Val Gly Thr Val Ala Ala Gly Arg
            195             200             205

Ile Gly Leu Ala Val Leu Arg Arg Leu Ala Pro Phe Asp Val His Leu
        210             215             220

His Tyr Thr Asp Arg His Arg Leu Pro Glu Ser Val Glu Lys Glu Leu
225             230             235             240

Asn Leu Thr Trp His Ala Thr Arg Glu Asp Met Tyr Pro Val Cys Asp
                245             250             255

Val Val Thr Leu Asn Cys Pro Leu His Pro Glu Thr Glu His Met Ile
                260             265             270

Asn Asp Glu Thr Leu Lys Leu Phe Lys Arg Gly Ala Tyr Ile Val Asn
            275             280             285

Thr Ala Arg Gly Lys Leu Cys Asp Arg Asp Ala Val Ala Arg Ala Leu
        290             295             300

Glu Ser Gly Arg Leu Ala Gly Tyr Ala Gly Asp Val Trp Phe Pro Gln
305             310             315             320

Pro Ala Pro Lys Asp His Pro Trp Arg Thr Met Pro Tyr Asn Gly Met
                325             330             335

Thr Pro His Ile Ser Gly Thr Thr Leu Thr Ala Gln Ala Arg Tyr Ala
            340             345             350

Ala Gly Thr Arg Glu Ile Leu Glu Cys Phe Phe Glu Gly Arg Pro Ile
            355             360             365

Arg Asp Glu Tyr Leu Ile Val Gln Gly Gly Ala Leu Ala Gly Thr Gly
        370             375             380

Ala His Ser Tyr Ser Lys Gly Asn Ala Thr Gly Gly Ser Glu Glu Ala
385             390             395             400

Ala Lys Phe Lys Lys Ala Val
            405
```

<210> SEQ ID NO 9

-continued

```
<211> LENGTH: 10
<212> TYPE: DNA
<213> ORGANISM: Escherichia coli
<220> FEATURE:
<221> NAME/KEY: misc_feature
<222> LOCATION: (1)..(10)
<223> OTHER INFORMATION: partial sequence from IpxC gene

<400> SEQUENCE: 9
cttccaggac                                                                   10
```